United States Patent [19]
Jones et al.

[11] Patent Number: 5,743,456
[45] Date of Patent: Apr. 28, 1998

[54] HAND ACTUABLE SURGICAL HANDPIECE

[75] Inventors: Christopher Scott Jones, Palo Alto; Phillip R. Sommer, Newark; Charles L. Nelson, Santa Clara, all of Calif.

[73] Assignee: Stryker Corporation, Kalamazoo, Mich.

[21] Appl. No.: 538,748

[22] Filed: Oct. 3, 1995

Related U.S. Application Data

[63] Continuation of Ser. No. 168,777, Dec. 16, 1993, abandoned.

[51] Int. Cl.⁶ .................................................. A61B 17/068
[52] U.S. Cl. ............................................. 227/176.1; 227/19
[58] Field of Search ............................... 227/19, 176, 177, 227/178, 180, 176.1, 177.1, 178.1, 180.1

[56] References Cited

U.S. PATENT DOCUMENTS

| | | |
|---|---|---|
| Re. 28,932 | 8/1976 | Noiles et al. |
| 3,275,211 | 9/1966 | Hirsch et al. |
| 3,819,100 | 6/1974 | Noiles et al. |
| 3,837,555 | 9/1974 | Green. |
| 3,949,924 | 4/1976 | Green. |
| 4,169,476 | 10/1979 | Hiltebrandt. |
| 4,196,836 | 4/1980 | Becht. |
| 4,204,623 | 5/1980 | Green. |
| 4,379,457 | 4/1983 | Gravener et al. |
| 4,391,402 | 7/1983 | Campbell et al. |
| 4,396,139 | 8/1983 | Hall et al. |
| 4,440,170 | 4/1984 | Golden et al. |
| 4,470,532 | 9/1984 | Froehlich. |
| 4,473,077 | 9/1984 | Noiles et al. |
| 4,520,817 | 6/1985 | Green. |
| 4,522,327 | 6/1985 | Korthoff et al. |
| 4,562,839 | 1/1986 | Blake, III et al. |
| 4,566,620 | 1/1986 | Green et al. |
| 4,580,712 | 4/1986 | Green. |
| 4,591,085 | 5/1986 | Di Giovanni. |
| 4,596,350 | 6/1986 | Smith et al. |
| 4,605,001 | 8/1986 | Rothfuss et al. |
| 4,606,344 | 8/1986 | Di Giovanni. |
| 4,607,636 | 8/1986 | Kula et al. |
| 4,632,290 | 12/1986 | Green et al. |
| 4,691,853 | 9/1987 | Storace. |
| 4,728,020 | 3/1988 | Green et al. |
| 4,741,336 | 5/1988 | Failla et al. |
| 4,752,024 | 6/1988 | Green et al. |
| 4,807,628 | 2/1989 | Peters et al. |
| 4,869,414 | 9/1989 | Green et al. |
| 4,915,100 | 4/1990 | Green. |
| 4,917,114 | 4/1990 | Green et al. |
| 4,938,408 | 7/1990 | Bedi et al. |
| 4,944,443 | 7/1990 | Oddsen et al. |
| 4,955,959 | 9/1990 | Tompkins et al. |
| 4,991,763 | 2/1991 | Storace. |
| 5,014,899 | 5/1991 | Presty et al. |
| 5,040,715 | 8/1991 | Green et al. |
| 5,042,707 | 8/1991 | Taheri ................................. 227/179 X |
| 5,065,929 | 11/1991 | Schulze et al. |
| 5,071,430 | 12/1991 | de Salis et al. |
| 5,084,057 | 1/1992 | Green et al. |
| 5,125,553 | 6/1992 | Oddsen et al. |

(List continued on next page.)

FOREIGN PATENT DOCUMENTS

| | | |
|---|---|---|
| 505 138 | 9/1992 | European Pat. Off. |
| 510 826 | 10/1992 | European Pat. Off. |

*Primary Examiner*—Rinaldi I. Rada
*Assistant Examiner*—Boyer Ashley
*Attorney, Agent, or Firm*—Flynn, Thiel, Boutell & Tanis, P.C.

[57] ABSTRACT

An inventive surgical handpiece comprises a handle unit and structure carried by the handle unit for engaging a patient. A hand actuable element is mounted for rotation on the handle unit, about first and second mutually transverse axes. A first mechanism is responsive to rotation of the hand actuable element about its first axis for imparting first degree of freedom movement to the patient engaging structure. A second mechanism is responsive to rotation of the same hand actuable element about its second axis for imparting second degree of freedom movement to the patient engaging structure.

24 Claims, 16 Drawing Sheets

U.S. PATENT DOCUMENTS

| | | |
|---|---|---|
| 5,137,198 | 8/1992 | Nobis et al. . |
| 5,161,725 | 11/1992 | Murray et al. . |
| 5,163,945 | 11/1992 | Ortiz et al. . |
| 5,171,247 | 12/1992 | Hughett et al. . |
| 5,174,487 | 12/1992 | Rothfuss et al. . |
| 5,289,963 | 3/1994 | McGarry et al. . |
| 5,312,023 | 5/1994 | Green et al. .......................... 227/19 X |
| 5,326,013 | 7/1994 | Green et al. .......................... 227/19 X |
| 5,328,077 | 7/1994 | Lou ...................................... 227/19 X |
| 5,348,259 | 9/1994 | Blanco et al. ....................... 227/19 X |
| 5,381,943 | 1/1995 | Allen et al. .......................... 227/19 X |

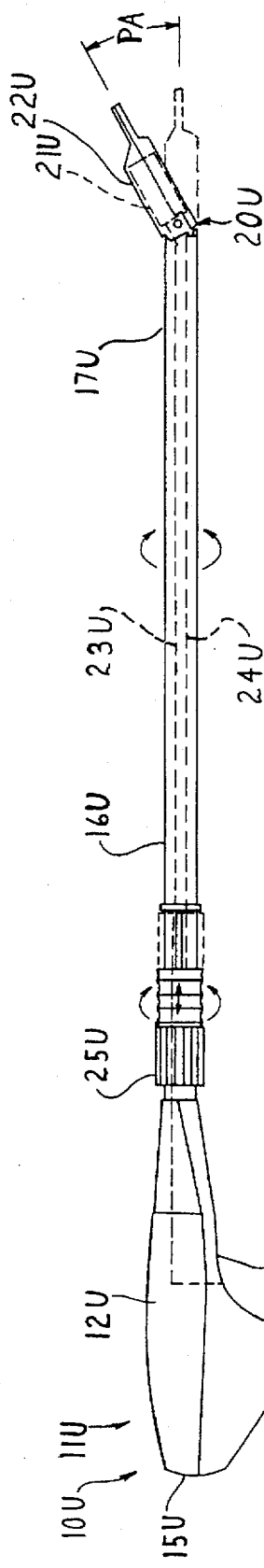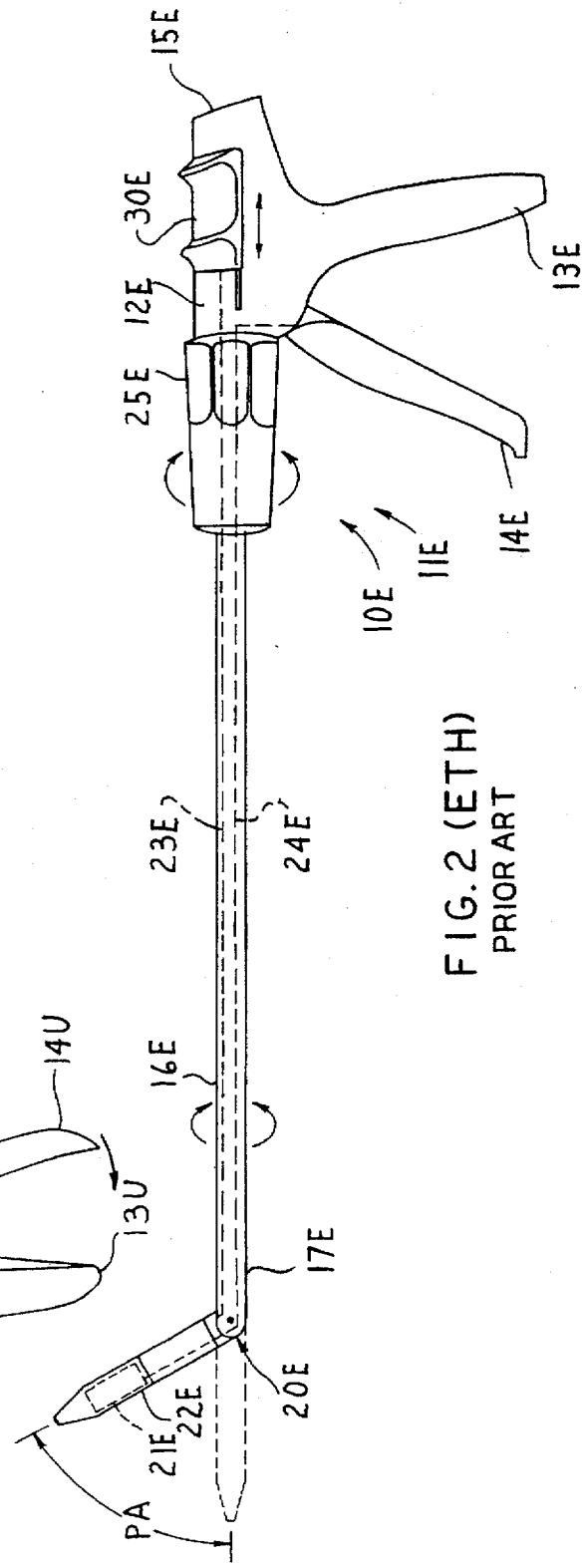
FIG.1 (USS) PRIOR ART
FIG.2 (ETH) PRIOR ART

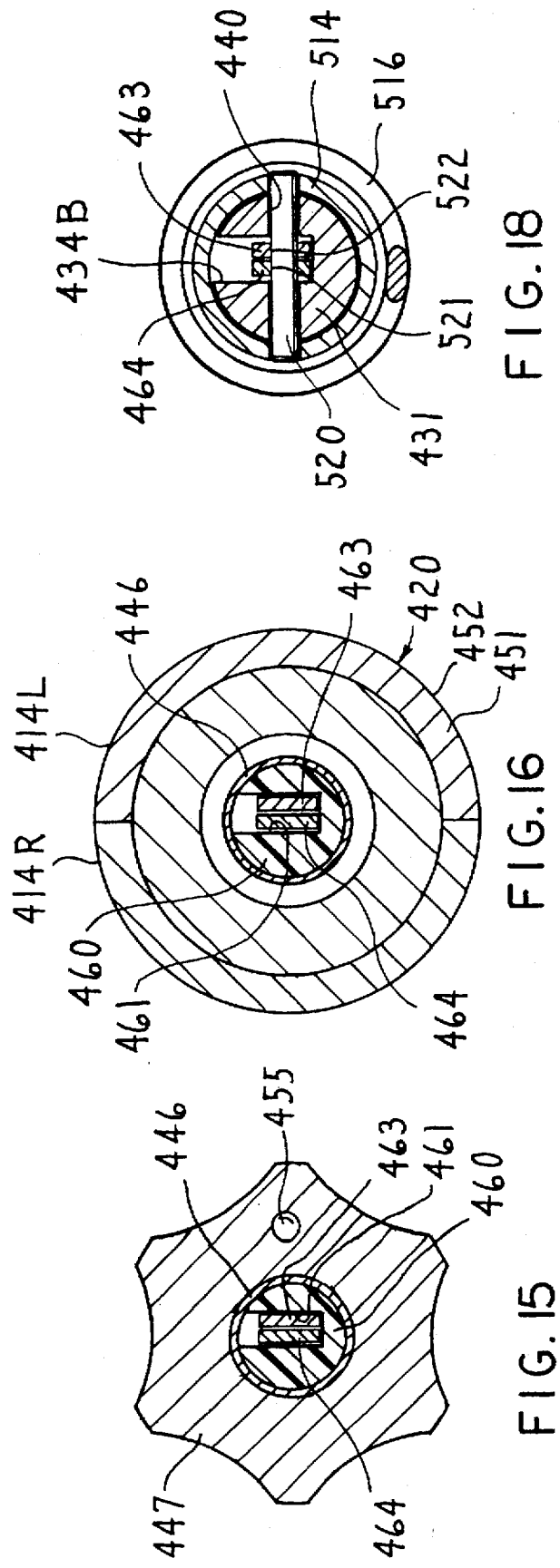

HAND ACTUABLE SURGICAL HANDPIECE

This application is a continuation of U.S. Ser. No. 08/168,177, filed Dec. 16, 1993, now abandoned.

FIELD OF THE INVENTION

This invention relates to a hand actuable surgical handpiece which is useable for endoscopic surgery, and more particularly to a surgical handpiece for applying fasteners, such as surgical staplers, to tissue of a patient.

BACKGROUND OF THE INVENTION

United States Surgical Corporation of Norwalk, Conn. and Ethicon, Inc. of Somerville, N.J. currently market respective laparoscopic hernia staplers 10U and 10E, shown schematically in FIGS. 1 and 2 respectively. Each comprises a pistol shaped handle unit 11U, 11E comprising a barrel 12U, E with a handgrip 13U, E and trigger 14U, E pendant from the barrel head of the rear end 15U, E of the barrel, and an elongate extension tube 16U, E extending coaxially forward from, and supported for rotation (roll motion) about its length axis with respect to, the barrel. An articulation pivot joint (pitch joint) unit 20U, E pivotly supports the casing 22U, E of a staple feeding and forming unit 21U, E with respect to the distal end 17U, E of the tube 16U, E. An elongate, rigid, pitch slider, schematically indicated at 23U, E, is operatively connected to the casing 22U, E of the staple feeding and forming unit through the pitch joint unit 20U, E and is longitudinally slidable in the tube 16U, E to change the pitch angle PA of the staple feeding and forming unit 21U, E with respect to the tube 16U, E. A second elongate, rigid slider, schematically indicated at 24U, E is longitudinally slidable in the tube 16U, E, beside the pitch slider 23U, E, and is operatively connected at its rear end to the trigger 14U, E and at its front end in an articulating manner through the pitch joint unit 20U, E to the staple feeding and forming unit 21U, E to cause staple feeding and forming in response to hand actuation of the trigger 14U, E. The tube 16U, E is rotatable about its longitudinal axis by a coaxially surrounding, manually rotatable, roll collar 25U, E located at the front end of the barrel 12U, E. Thus, a first hand of the user grips the handgrip 13U, E and trigger 14U, E and a second hand is needed to rotate the roll collar 25U, E.

The above-discussed features are present in both the mentioned United States Surgical and Ethicon laparoscopic hernia staplers 10U, E.

However, the two staplers 10U, E differ in their manual actuation of pitch joint articulation, to change the angle PA of the staple forming and feeding casing 22U, E with respect to the length axis of the elongate tube 16U, E.

More particularly, in the United States Surgical stapler 10U (FIG. 1), the roll collar 25U is also axially movable along the tube 16U, toward and away from the front end of the barrel 12U, by the second hand of the user, and is operatively connected to the pitch slider 23U, to change the pitch angle PA of the staple feeding and forming casing 22U with respect to the tube 16U.

On the other hand, in the Ethicon stapler 10E (FIG. 2) a saddle 30E straddles and is manually movable longitudinally along the top central part of the barrel 12E, ahead of the hand grip 13E and trigger 14E, and is operatively connected to the pitch slider 23E to change the pitch angle PA of the staple feeding and forming casing 22E with respect to the tube 16E. The saddle 30E is conveniently moveable by the second hand of the user, as in the United States Surgical stapler 10U, and is less conveniently actuable by a hand gripping the handgrip 13E to pull the trigger 14E.

Thus, both the United States Surgical and Ethicon staplers 10U and 10E require, as a practical matter, two hands to operate if roll and/or pitch adjustments are to be made.

The objects and purposes of the present invention include provision of a surgical handpiece capable of one handed operation, namely of one-handed actuation of (1) attitude adjustment about a first axis and (2) attitude adjustment about a second axis and (3) initiation of patient tissue treatment, for example of one-handed actuation of (1) pitch adjustment, (2) roll adjustment and (3) a trigger.

SUMMARY OF THE INVENTION

An inventive surgical handpiece comprises a handle unit and structure carried by the handle unit for engaging a patient. A hand actuable element is mounted for rotation on the handle unit, about first and second mutually transverse axes. A first mechanism is responsive to rotation of the hand actuable element about its first axis for imparting first degree of freedom movement to the patient engaging structure. A second mechanism is responsive to rotation of the same hand actuable element about its second axis for imparting second degree of freedom movement to the patient engaging structure.

Other objects and purposes of the invention will be apparent to persons acquainted with apparatus of this general type upon reading the following specification and inspecting the accompanying drawings.

BRIEF DESCRIPTION OF THE DRAWINGS

FIG. 1 is a schematic, partially broken, side elevational view of a laparoscopic hernia stapler marketed by United States Surgical Corporation.

FIG. 2 is a similar view of a laparoscopic hernia stapler marketed by Ethicon Corporation.

FIGS. 3–11C rather schematically show an example of an available, on the market, pitch joint unit and staple feeding and forming unit, corresponding to that employed in the FIG. 2 Ethicon marketed hernia stapler.

More particularly, FIG. 3 is a fragmentary, partly broken pictorial view rather schematically showing the such pitch joint unit straight and prior to trigger actuation, FIG. 3 being partially broken to show the pitch causing structure.

FIG. 4 is a view similar to FIG. 3 but with such pitch joint unit angled (bent).

FIG. 5 is a view similar to FIG. 3 but additionally showing structure in such pitch joint unit for transferring trigger actuation motion to actuate staple forming and feeding in the staple feeding end forming unit, such structure including the staple forming and feeding (second) slider, such second slider being rearwardly positioned.

FIG. 6 is a view similar to FIG. 5 but partly exploded and with such second slider forwarded, on completion of trigger pull and at the end of staple formation.

FIG. 7 is a view similar to FIG. 6 but with the articulation joint bent.

FIG. 8 is an enlarged exploded, pictorial view rather schematically showing such staple feeding and forming unit.

FIG. 9 is a view similar to FIG. 8 but with such unit assembled.

FIGS. 11A and 11B and 11C are cross-sectional views taken substantially on the line 11—11 of FIG. 11C showing three further operating positions, for forming the FIG. 10C staple to grip patient tissue and to ready the formed staple for release from staple feeding and forming unit.

FIGS. 15 through 21 are sectional views substantially taken on the corresponding lines 15—15 through 21—21, respectively, of FIG. 14.

DETAILED DESCRIPTION

FIGS. 12–23 show a hand actuable, surgical handpiece 400 embodying the present invention. The inventive handpiece 400 includes at its rear or proximal end (rightward end in FIG. 12), a handle unit 411 adaptable for actuating a variety of distally located surgical tools for performing work on a patient.

Figure 12:
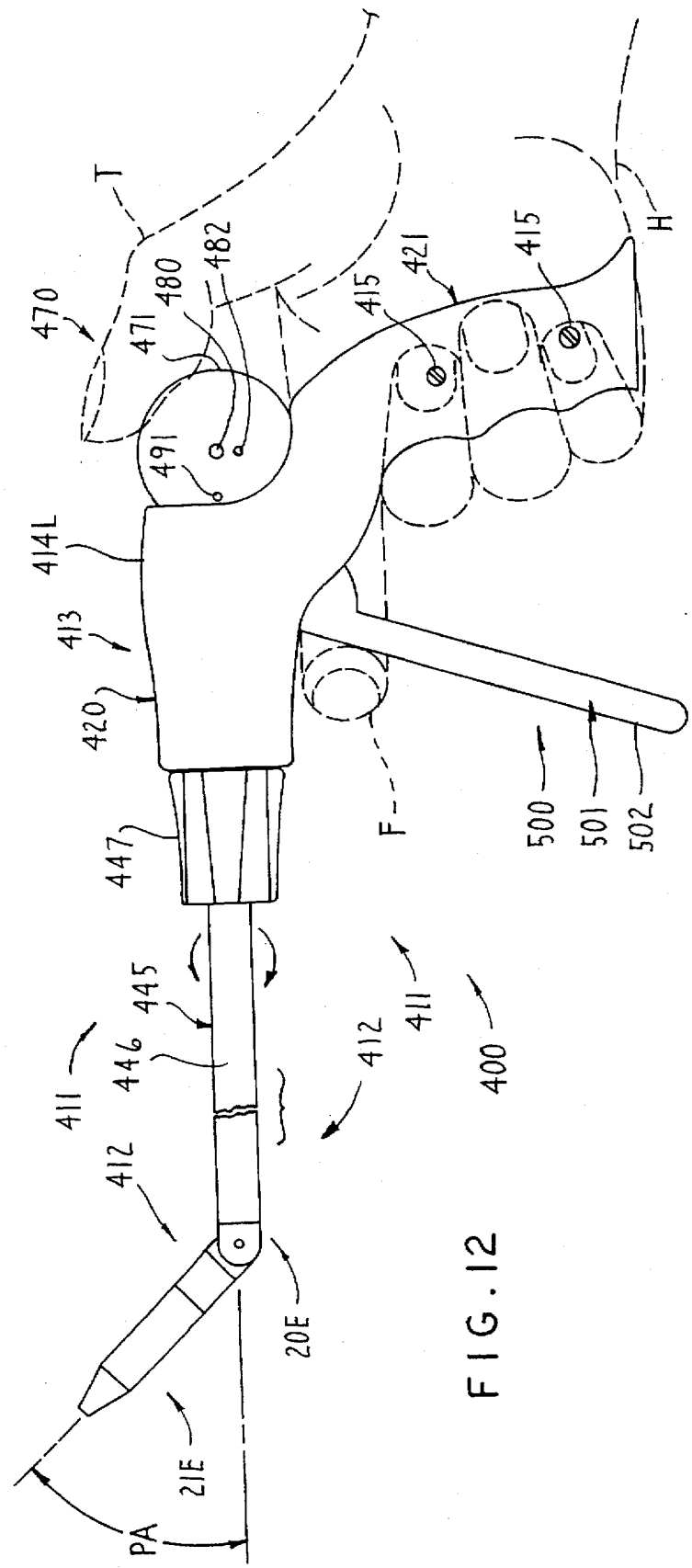
FIG. 12 is a side elevational view of a hand actuable, surgical handpiece, for example a laparoscopic stapler, embodying the present invention.

One such tool is schematically illustrated at 412 in FIG. 12. In the example here illustrated, the FIG. 12 tool 412 may be the distal portion of a laproscopic stapler, here a staple feeding and forming unit connected by a pitch joint unit to Applicants'inventive handle unit 411. It is convenient to illustrate such a staple feeding and forming unit and pitch joint unit in terms of the available, on the market, pitch joint unit 20E and staple feeding and forming unit 21E of the FIG. 2 Ethicon marketed hernia stapler.

Handle Unit 411 (FIGS. 12–23)

Figure 13:
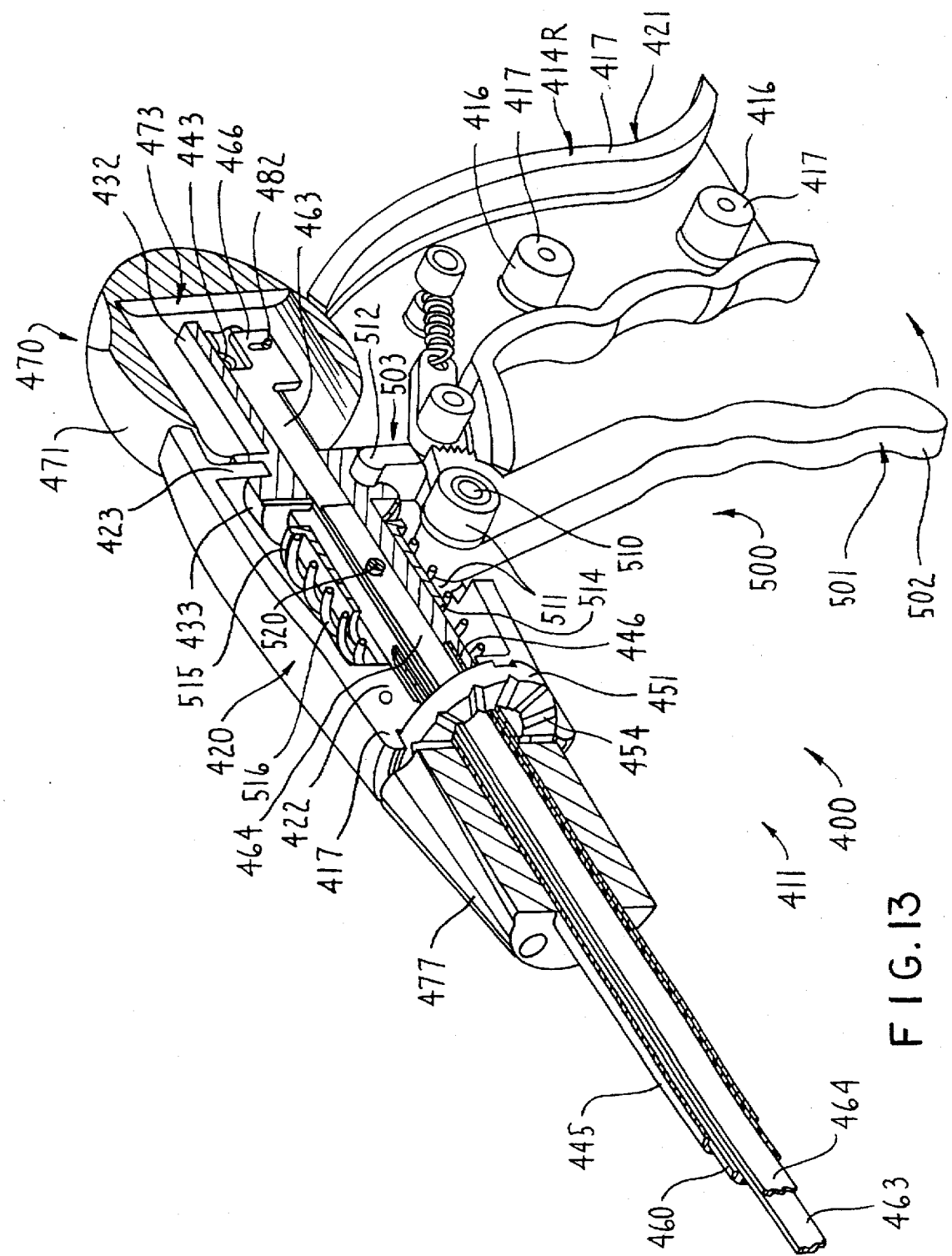
FIG. 13 is an enlarged fragmentary pictorial view, partly in central cross-section, of the handle unit of the FIG. 12 handpiece.

The handle unit 411, embodying the present invention, comprises a frame, here in the form of a housing 413 (FIGS. 12 and 13). The housing 413 is hollow and is preferably formed of a rigid material as two laterally opposed, concave, half shells, namely a left half shell 414L (FIG. 12) and right half shell 414R (FIG. 13). The shells 414L and 414R are fixed together, in the finished handpiece 400, by any convenient means, such as adhesive bonding, screws 415 threaded in bosses 416 located inside right housing half shell 414R (FIG. 13), and/or the like. In any event, the housing half shells have opposed faces 417, which upon assembly of the half shells to form the housing 413 are in contact and may serve as adhesive contact surfaces in a conventional manner.

The housing 413 comprises a barrel 420, from the rear end portion of which depends a fixed handgrip 421. Front and rear bulkheads 422 and 423 (FIGS. 13, 14 and 17) extend radially inward from the peripheral wall 424 of the barrel 420 adjacent the front and rear ends of the barrel in axially spaced relation from each other. The bulkheads 422 and 423 take the form of inwardly extending annular flanges and have respective central openings 425 and 426 coaxial with the longitudinal axis of the barrel 420. It will be understood that the bulkheads 422 and 423 are here split along the central vertical plane of the barrel, along with the rest of the barrel 424, such that left and right halves of the central openings 425 and 426 are formed in opposite ones of the left and right half shells 414L and 414R.

Figure 14:
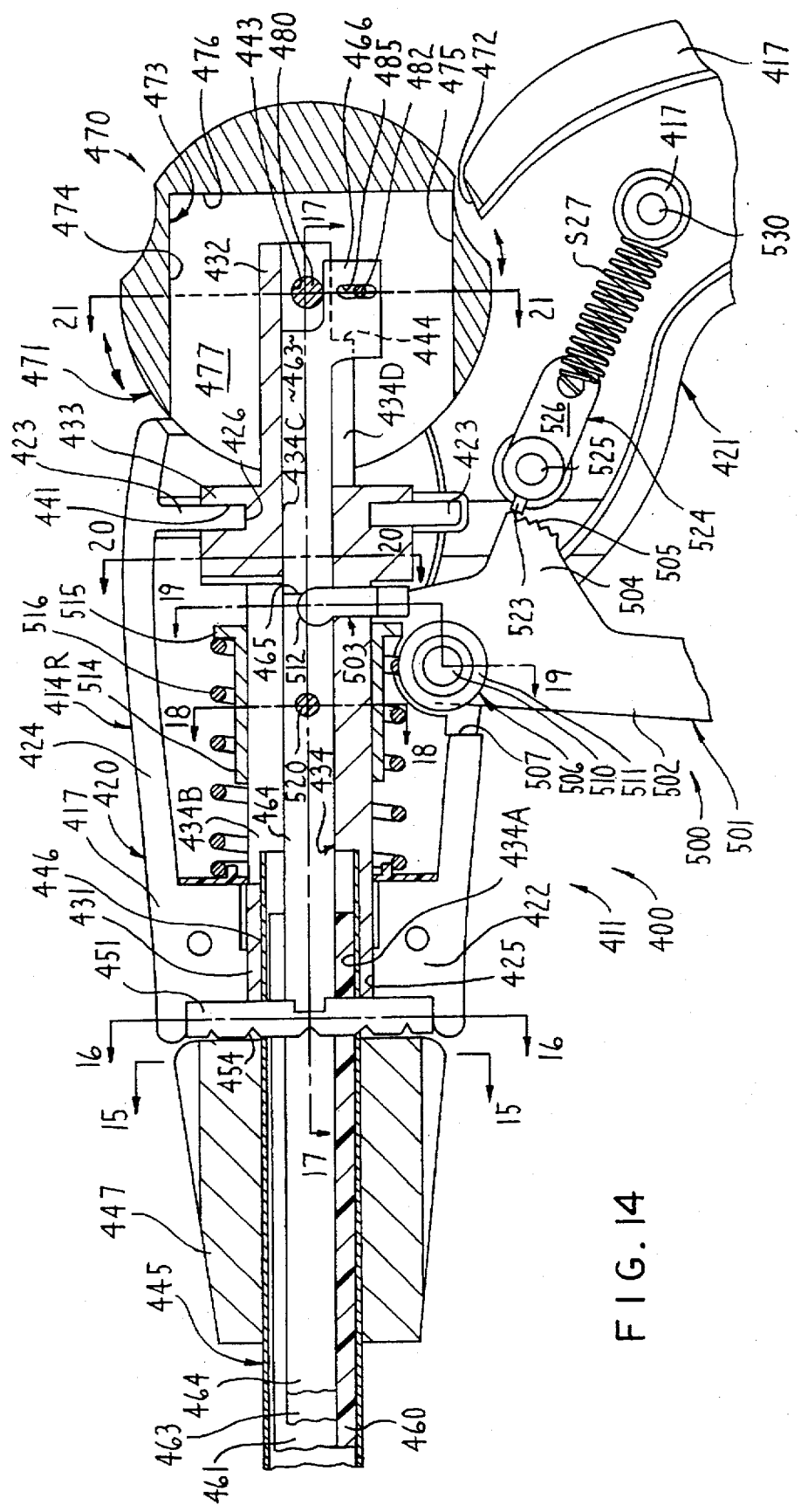
FIG. 14 is an enlarged, fragmentary, central cross-sectional view, in side elevation, of the FIG. 13 handle unit.
Figure 21:
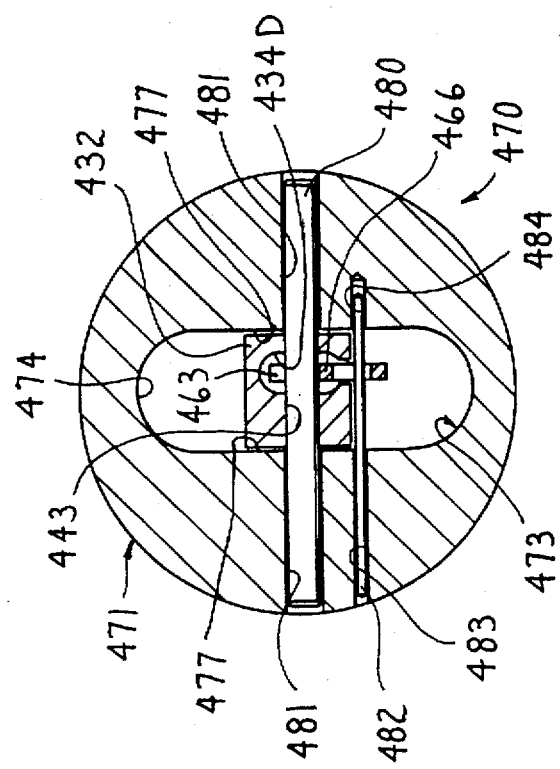
Figure 20:
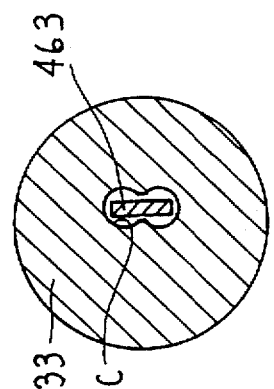

An elongate rotor 430 (FIGS. 13, 14 and 22) comprises an elongate, hollow, tubular cylindrical front portion 431, an elongate, generally rectangular cross-section, cylindrical rear portion 432 and, axially interposed therebetween, a coaxial, radially outward extending, generally cylindrical, drum-like intermediate portion 433. The central passage 434 extends coaxially through the rotor 430 as seen in FIG. 14. The passage 434 varies in cross-sectional configuration along its length as shown in FIGS. 14 and 17–21. More particularly, the passage 434 comprises (1) a wide, cylindrical, circular cross-section, forward opening recess 434A (FIGS. 14 and 22) communicating rearwardly with (2) an intermediate, narrow width, rectangular cross-section, axially elongate, radially deep groove 434B which opens radially through one portion of the peripheral wall of the rotor 430 (FIGS. 14, 18, 19 and 22), in turn communicating rearwardly with (3) a substantially 8-shaped cross-section passage portion 434C (FIGS. 14, 17 and 20), which in turn communicates with (4) a rearward extension 434D. Passage rearward extension 434D is a slot which opens radially through the peripheral wall of the rotor rear portion 432 in a radial direction opposite the radial opening of the groove 434B (FIGS. 14 and 21). The slot 434D also opens rearwardly as seen in FIG. 14. The 8-shaped passage portion 434C and slot 434D are slightly radially offset to one side (the right side in FIGS. 20 and 21) of the central plane of the rotor.

Figure 17:
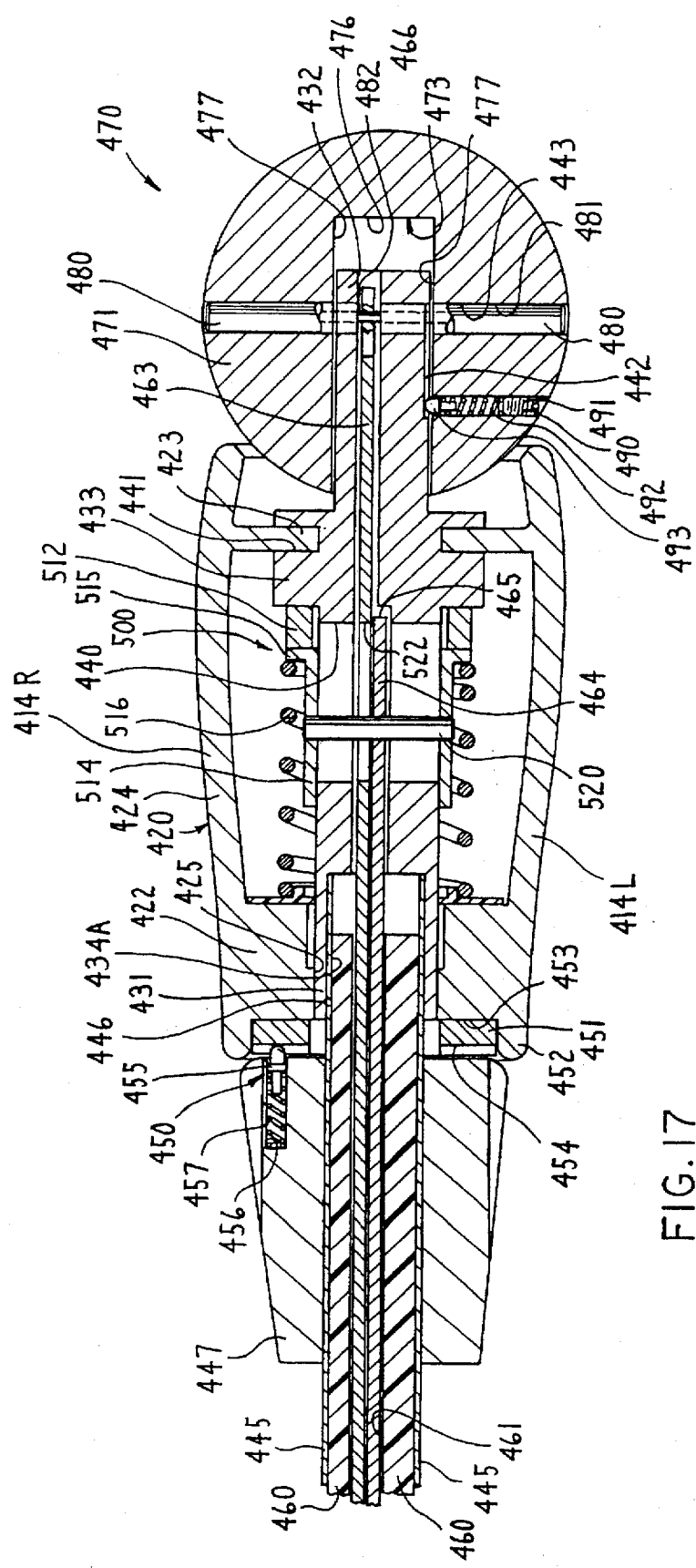
Figure 22:
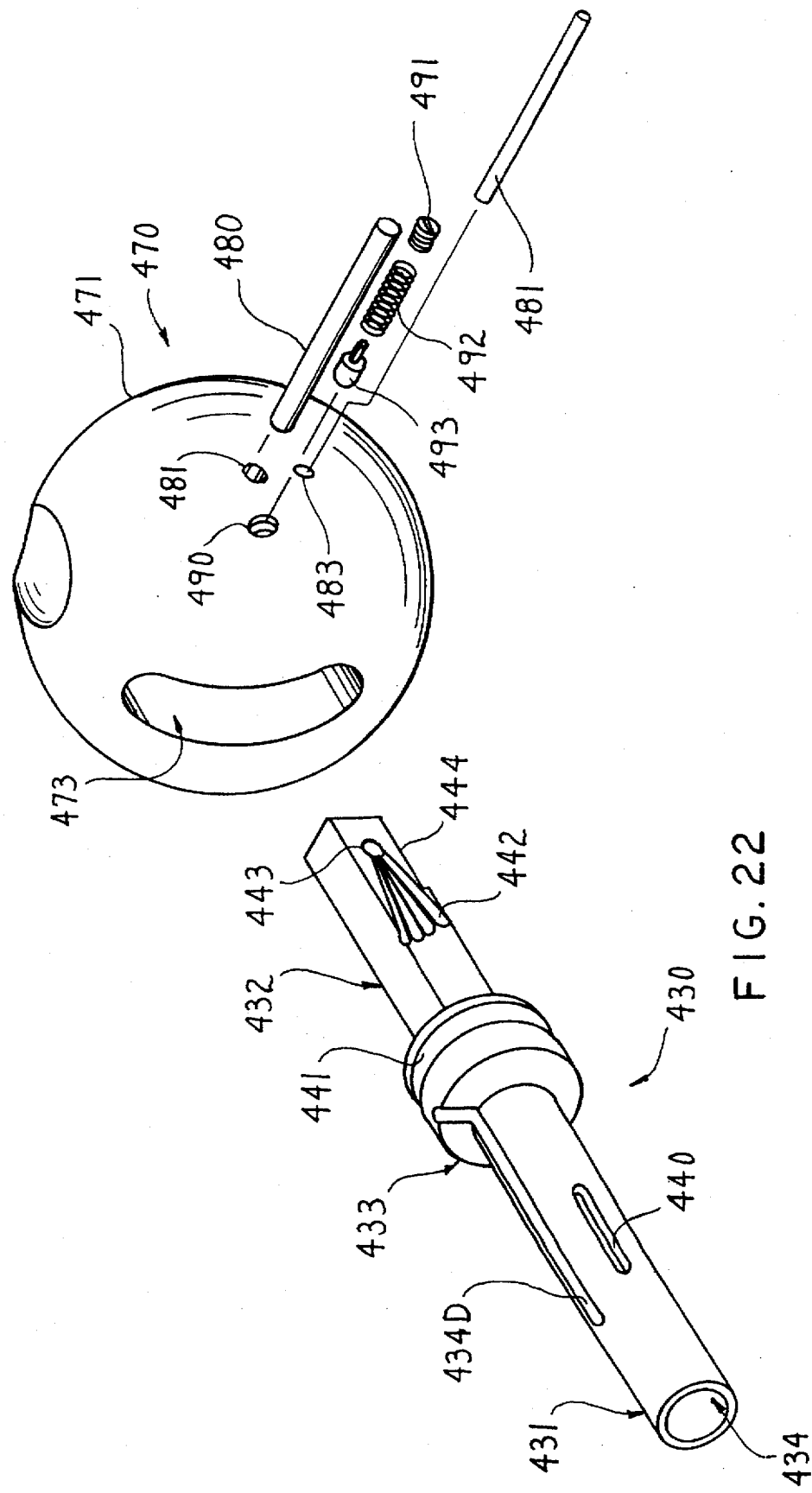
FIG. 22 is an exploded pictorial view of the rotor and slider of FIGS. 12 through 14 and 17 through 19 and 21.
Figure 23:
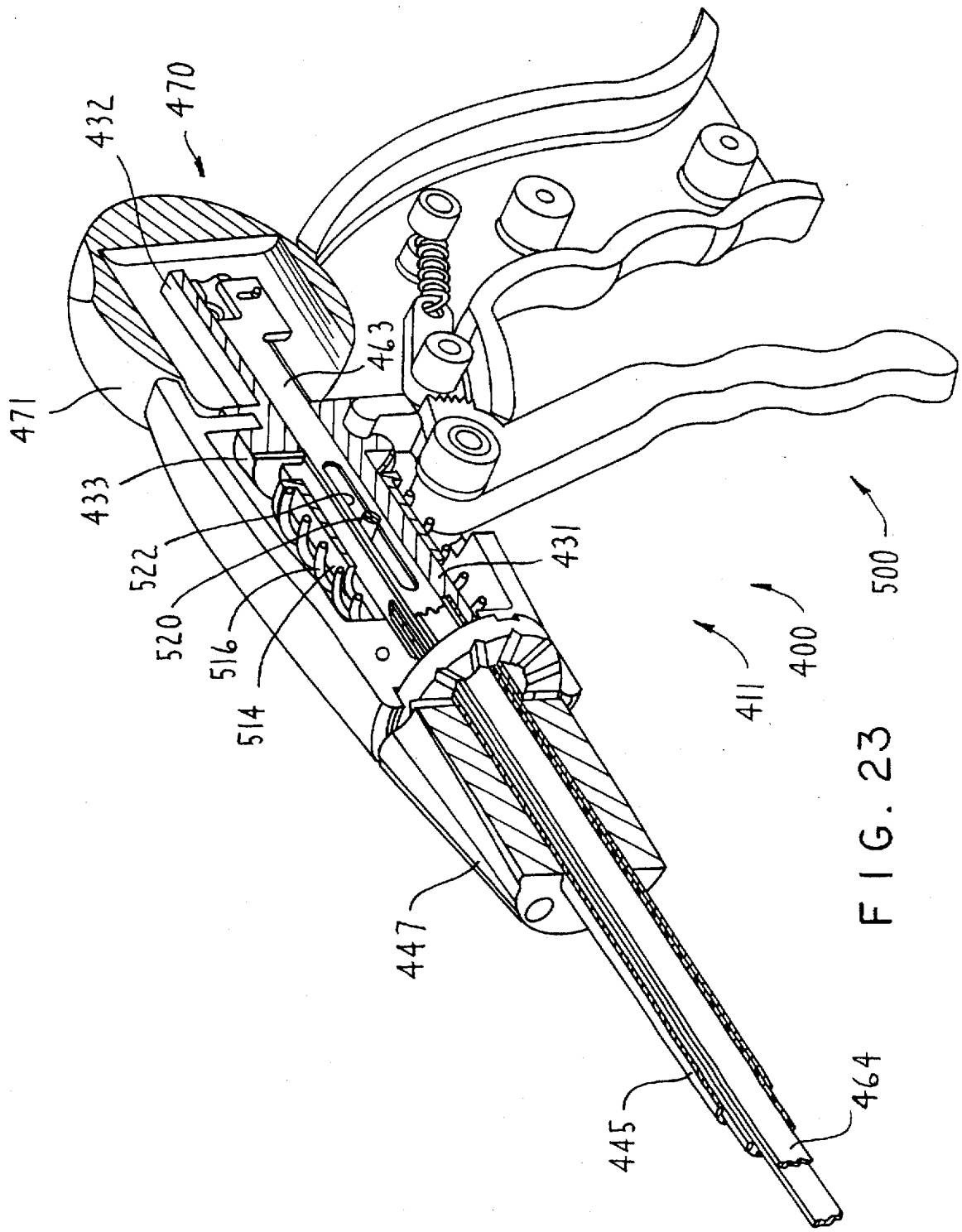
FIG. 23 is a view similar to FIG. 13 but with the rear portion of the trigger actuated second slider removed to better show the pitch slider.

The rotor 430 includes an axially elongate slot 440 (FIGS. 17, 18 and 22) which extends diametrally across the groove 434B to open on opposite sides of the rotor front portion 431. The drum-like intermediate portion (or drum) 433 of the rotor 430 has a coaxial annular groove 441 in the periphery thereof as seen in FIGS. 14, 17 and 22. The rotor rear portion 432 has, on one side thereof (the near side in FIG. 22) a plurality (here four) of forwardly divergently angled, shallow detent grooves 442. A lateral through hole 443 (FIGS. 14, 17, 21 and 22) extends laterally through the rotor rear portion 432 near the rear end thereof, the detent grooves 443 here converging rearwardly to the lateral through hole 443. The bottom (in its orientation of FIG. 22) of the rotor rear portion 432 is relieved at 444.

The rotor 430 is located for coaxial rotation in the barrel 420 by radial support of rotor front portion 431 in the barrel annular front bulkhead 422 and by radial and axial support of the drum 433 by reception in its annular groove 441 of the rear bulkhead 423 of the barrel 420. The rotor 430 is readily assembled in the barrel 420 by laterally laying it in the right housing half shell. 414R, as seen in FIG. 14, and then laying left housing half shell 414L thereon to provide the closed housing shell of FIG. 12. The rotor is thus fixed for rotation within the barrel 420.

The rotor 430, like the housing 413, is of a rigid material.

An elongate, thin wall, rigid metal tube 445 is fixed to and extends coaxially forward from the rotor 430, for rotation therewith, as seen in FIG. 14. The rotation of the rotor 430 and tube 445 is about their common central axis and may be referred to as "roll" motion. The rear end portion 446 of the tube 445 is fixed by a convenient means, such as brazing or adhesive bonding, snugly within the front opening recess 434A of the rotor 430.

A forward tapering, axially fluted, roll collar 447 is snugly telescoped over and fixed by an convenient means, such as adhesive bonding, to the tube 445, adjacent the front end of the barrel 420. The rotor 430, tube 445 and roll collar 447 thus are rotatable together in mutually fixed relation.

A resilient roll detent assembly 450 (FIG. 17) resiliently fixes the roll collar 447 and hence the rotor 430 and tube 445 in any one of several angularly spaced rotative positions with respect to the barrel 420, wherein the rotor 430, tube 445 and roll collar 447 can easily be hand rotated between such angularly spaced positions against a modest resilient detent drag. The detent assembly be of any desired type and here includes a disc-like detent ring 451 (FIGS. 14, 16 and 17) loosely coaxially surrounding the tube 445 and coaxially fixed by any convenient means, such as mechanically or by adhesive bonding, to the front end of the barrel 420. In the embodiment shown, the front end of the barrel has a coaxial, forward extending annular lip 452 (FIG. 17) defined by dishing the front end of the barrel, as indicated at 453, to assist in coaxially locating the ring 451 with respect to the centerline of the barrel and tube 445. Plural, circumferentially spaced, radially extending, forward facing detent grooves 454 indent the front face of the detent ring 451. The grooves 454 are preferably shallow, V cross-section grooves. The detent ring 451 is of rigid material. Indeed, it is contemplated that the detent ring 451 might be formed integrally in the front end of the barrel 420.

The detent assembly 450 further includes a detent finger 455 axially slidable in a rear opening, blind guide hole 456 located in the rear (rightward in FIG. 17) face of the roll collar 447 and spaced radially outward of the tube 445. A compression spring 457 in the blind hole 456 urges the finger 455 rearwardly against the front face of the detent ring 451 so as to drop the finger 455 rearwardly into successive ones of the detent grooves 454 of the detent ring 451, as the roll collar 447 and tube 445 are rotated with respect to barrel 420, so as to tend to gently resiliently maintain the tube 445 and roll collar 447 in defined circumferentially spaced positions with respect to the barrel 420. This resiliently permits rotation, by the user, of the tube 445 and roll collar 447 with respect to the barrel 420, generally in the manner described with respect to roll collars 25U and 25E of FIGS. 1 and 2.

A rigid slider guide 460 (FIGS. 14–17) is fixed within and substantially fills the tube 445, almost from end to end of the tube. The guide 460 is fixed, by an convenient means, for example by adhesive bonding, shrink fit, or the like, within the tube 445. A deep, radial guide groove 461 (FIGS. 14–17) opens radially outward through one side of the slider guide 460. The guide groove 461 in the slider guide 460 radially coplanar with the passage groove 434B in the rotor 430 and opens in the same radial direction. The guide groove 461 thus forms an axial extension of the rotor groove 434B.

Elongate, substantially plate-like, preferably rectangular cross section sliders, namely a first (or pitch) slider 463 and a second (or tool actuation) slider 464, are longitudinally slidably disposed side-by-side in the guide groove 461 in the tube 445 and extend rearward into the rotor groove 434B. The slider 463 is located behind the second slider 464 in FIG. 14. Whereas the second slider 464 extends rearward almost to the rear end of the groove 434B, as indicated at 465 in FIG. 14, the pitch slider 463 extends rearward therebeyond, through the passage portion 434C and almost to the rear end of the rotor 432. The pitch slider 463 has a dropped, rear end portion, or downward dog leg 466 (FIG. 14). The dog leg 466 lies below (FIG. 14) the level of the lateral hole 443 in the rear end portion 432 of the rotor 430 and extends radially out through the slot 434D.

A roll/pitch actuator assembly 470 (FIG. 14) includes a multi-pivot member 471 pivotable about first and second mutually transverse axes with respect to the handle unit 411, which multipivot member 411 is a rigid, rounded member which is preferably ball shaped and for convenience is hereafter referred to as the ball 471. The ball 471 is loosely disposed in an opening 472 in the rearward, upper portion of the handle unit 411, namely at the rear of the barrel 420 and upper end of the handgrip 421. Thus, as seen in FIGS. 12–14, the ball 471 is exposed rearwardly, sidewardly and upwardly for engagement by the thumb of a hand holding the handgrip 421. The ball 471 has a central chamber 473 which, in in orientation shown in FIGS. 13 and 14, is generally rectangular, indeed almost square, in elevation. The chamber 473 occupies much of the height and forward/ rearward portion of the ball 471. The chamber 473 is relatively narrow laterally (looking into the page in FIG. 14), having relatively narrow top, bottom and rear walls 474, 475 and 476 connecting substantially parallel sidewalls 477. The chamber 473 opens general forwardly into the rear portion of the barrel 420 (FIG. 14) and receives therein the rear portion 432 of the rotor 430.

The central part of a pitch pivot shaft 480 (FIGS. 12, 14, 17 and 21) extends rotatably, coaxially and transversely through the lateral hole 443 (FIG. 14) in the rear portion 432 of the rotor 430. The ends of the shaft 480 are fixed in holes 481 coaxially aligned on a diameter of the ball 471 and which open perpendicularly through the sidewalls 477 of the chamber 474. In the position of the parts shown on the drawings, the shaft 480 extends horizontally in FIG. 21 and extends into the page in FIG. 13. The shaft 480 is fixed in the diametral holes 481 of the ball by any convenient means, such as press fit, adhesive bonding, etc. The ball 471 is thus fully mounted for forward/rearward (pitch) rotation on the rear portion 432 of the rotor 430. Clearance between the chamber sidewalls 477 and the rotor rear portion 432 is snug but permits such pivoting in pitch of the ball with respect to the rotor, as generally indicated in FIG. 21. As indicated in FIG. 14, the rotor rear portion 432 substantially clears vertically both the top wall 474 and bottom wall 475, of the ball chamber 473, and also substantially clears the rear wall 476 thereof. Accordingly, the ball 471 can pivot in pitch through substantial angles both clockwise and counterclockwise with respect to the rotor rear end portion 432, namely until the forward ends of the top and bottom chamber walls 474 and 475 collide with the top and bottom of the rotor rear portion 432. This permits pitch rotation through an angular range of about 90° to 110°.

Spaced below the pitch pivot shaft 480 (FIGS. 14 and 21) is a parallel pitch drive pin 482. The pitch drive pin 482 passes through a hole 483 in one side (the left in FIG. 21) of the ball, extends across the chamber 473 and lodges in a blind hole 484 in the opposite (right in FIG. 21) sidewall 477 of the ball 471. The pitch drive pin 482 is rigid and fixed with respect to the ball 471 by any convenient means, such as adhesive bonding, press fit, etc.

The dog leg 477 of the pitch slider 463 has an upstanding (in the position of the parts in FIG. 14) slot 485 through which the pitch drive pin 482 laterally extends. The slot 485 is narrow in the longitudinal direction of the pitch slider 463, namely a close clearance fit on the pitch drive pin 482. However, the slot 485 is several diameters (here about four) times vertically longer than its lateral width. As a result, forward/rearward (pitch) pivoting of the ball, about the pivot shaft 480, rotates the pitch drive pin 482 eccentrically, namely along a portion of a circle centered on the axis of the shaft 480, with a vertical component of motion permitted by the vertical elongation of the slot 485 and with the horizontal component of motion which longitudinally moves the pitch slider 473 forward and rearward along the common longitudinal axis of the pitch slider, rotor and tube 445. This forward and rearward reciprocation of the pitch slider 463 can be employed to pivot a tool on the forward end of the tube 445, for example as above discussed with respect to the FIG. 2 (Ethicon) pitch slider 23E sliding toward and rearward to change the pitch angle PA of the Ethicon staple feeding and forming unit 21E.

Referring to FIG. 22, the above-mentioned detent grooves 442, diverging forwardly from the lateral through hole 443 in the rear portion 432 of the rotor, are a part of a pitch detent assembly, which further includes a hole 490 extending parallel to the hole 483 and into the ball side (left side in FIG. 21). A set screw 491 threaded into the outer portion of the hole 490 retains a compression spring 492 in the hole 490. The spring 492 resiliently urges inward, toward the chamber 473 of the ball 471 a detent finger 493. The hole 490 and set screw 491 are, in the pitch centered position of the ball in FIGS. 12, 14, 21 and 22, spaced horizontally in front of the pitch pivot shaft 480 and thus in direct opposition to the forward portion of the forwardly diverging detent grooves 442 (FIG. 22). Accordingly, the finger 493 is spring urged into the opposed one of the grooves 442 to gently resiliently hold the forward/rearward position of the pitch slider 463 and the forward/rearward pivot position of the ball 471. However, a modest forward/rearward pivoting force on the ball 471 suffices to overcome the spring force holding the finger 493 in one of the grooves 442 and allows the finger to be moved up or down across the grooves, thereby allowing the ball to displace pivotally forward or rearward (clockwise or counterclockwise as seen from the side thereof in FIG. 14), so as to displace the pitch slider 463 correspondingly forward or rearward to change the pitch angle PA (FIG. 12).

The ball 471 is also pivotable about a second axis transverse to the pitch pivot axis defined by the shaft 480. More particularly, this second axis is the above discussed roll axis of the rotor 430, tube 445 and roll collar 447.

Thus, while gripping the handgrip 421, the user can apply the thumb T (FIG. 12) of the same hand H to the upper and rearward portion of the ball 471. Moving the thumb T sideways pivots the ball 471 from side-to-side and results in rotation of the roll collar 447 and tube 445, along with the tool 412 at the distal end of the tube 445, resulting in roll rotation of the pitch joint unit 20E and staple feeding and forming unit 21E in the particular example shown in FIG. 12. The same thumb T can rotate the ball 471 forwardly and rearwardly about the axis of the shaft 480 to move the pitch slider 463 (FIG. 14) forwardly and rearwardly. This forward/rearward movement of the pitch slider 463 can be used in the manner of the pitch slider 23E of the FIG. 2 Ethicon device to change the pitch angle PA of the patient engaging unit 21E. The hand H gripping the handgrip, can instead reach up with both forefinger and thumb, and grip, and rotate the ball.

Thus in contrast to the U.S. Surgical and Ethicon units of FIGS. 1 and 2, the handpiece 400 embodying the present invention can be fully actuated with just one hand H and both pitch and roll actuation can be carried out with the same portion of the that one hand, namely the thumb T of the hand H supporting the handgrip.

Attention is directed to the tool actuating unit 500 of the handpiece 400. The tool actuating unit 500 includes the above-described second slider 464, forward/rearward sliding movement of which can be used to actuate a tool, for example actuate a staple forming and feeding unit like the unit 21E of the FIG. 2 Ethicon apparatus, and to do so for example through a pitch joint like that at 20E in the FIG. 2 Ethicon device namely in the manner of the Ethicon second slider 24E the above discussed.

The tool actuating unit 500 further includes a trigger 501 (FIGS. 12 and 13). The trigger 501 includes a lower end portion 502 (FIG. 12) actuatable by one or more fingers F of a hand holding the handgrip 21, an upper end portion in form of a yoke 503 (FIGS. 13 and 14), a rearwardly extending arm 504 with rear facing ratchet teeth 505 (FIG. 14), and a pivot 506 intermediate the ends of the trigger for pivoting the trigger 502 with respect to the housing 413 in spaced relation below the rotor 430. The lower end portion, or finger engageable portion, 502 of the trigger protrudes downwardly loosely through an opening 507 in the bottom of the housing 413 and more particularly in the bottom of the barrel 420, beneath the rotor 430. The trigger lower end portion 502 may be straight as in FIG. 12 or somewhat contoured to conform to the finger of the user, as in FIG. 13. The pivot 506 may be of any convenient type, for example including a cross shaft 510 extending transversely through the trigger 501 and supported by bosses 511 fixed with respect to the opposed left and right half shells 414 of the housing 413. In any event, the motion of the trigger 501 is conventional, namely finger pull by the user moves it rearwardly toward the handgrip 421 as generally indicated by the adjacent arrow.

Figure 19:
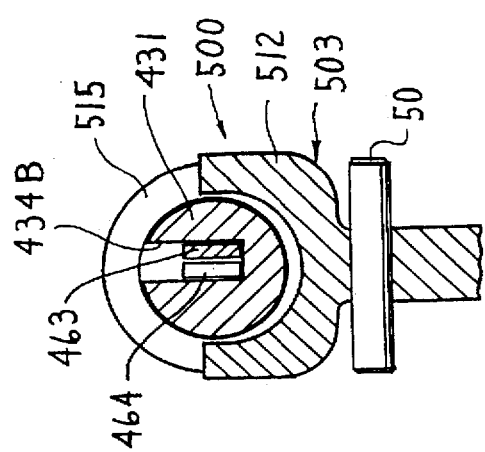

The yoke 503 is of upward opening substantially U-shape, comprising a laterally spaced pair of rigidly interconnected, upstanding arms 512 (FIGS. 13, 17 and 19).

The rotor front portion 431, between the drum 433 and the barrel front bulkhead 422 is of cylindrical periphery and snugly axially slidably supports thereon a generally tubular spool 514 having a radially outwardly extending flange 515 at its rear end. The front end of the spool 514 is well spaced rearward from the bulkhead 422 of the housing, in the relaxed, starting position of the apparatus shown in FIG. 14. The arms 512 extend upward, straddling the central portion of the rotor 430, and the upper ends of the arms 512 bear against the rearward end of the spool 514 at the rear annular flange 515 thereof. A large coil compression spring 516 coaxially surrounds the spool 514 and is axially trapped between the housing bulkhead 422 and the spool flange 515, so as to urge the spool 514 rearwardly to press the tops of the arms 512 rearwardly toward the adjacent drum 433.

A cross shaft 520 (FIGS. 14, 17 and 18) rigidly fixes the spool 514 to the second slider 464. In the position of the parts shown in the drawings, the cross shaft 520 is horizontal (see particularly FIG. 18) and is diametrally located with respect to the spool 514 and the rotor 430. The cross shaft 520 has ends fixed by any convenient means such as a press fit, adhesive bonding, etc. in diametral through holes in the spool 514. The shaft 520 passes snugly through the hole 521 in the second slider 464. Axial motion of the second slider 464, the spool 514, and cross shaft 520 is permitted by passage of the cross shaft 520 through axially elongate, diametrally opposed slots (namely the aforementioned slots 440 in FIG. 17) in the front portion 431 of the rotor 430 as well as through a corresponding axially elongate slot 522 (FIGS. 17, 18 and 23) laterally through the pitch slider 463. The slots 440 and 522 are axially elongate sufficiently to permit the desired full axial range of travel of the spool 514 and attached second slider 464 and cross shaft 520, regardless of the axial position of the pitch slider 463, in response to forward/rearward pivoting of the ball 471. The contact between the arms 512 and the spool flange 515 permits roll motion (rotation about its longitudinal axis) of the rotor with the ball 471, independent of the position of the trigger 501 and hence of the arms 515.

In the embodiment shown, a rearward pull on, and displacement of, the trigger 501 causes the arms 515 to push forward the spool 514 and hence the second slider 64 for actuation of a surgical tool at the front end of the tube 445, for example actuation through a pitch joint unit 20E of a staple forming and feeding unit 21E.

The rear arm 504 of the trigger has its ratchet teeth 505 opposing a radially protruding tab 523 (FIG. 14) of a pawl 524 pivoted at 525 on the handgrip 421. The pawl, 526, is urged generally rearwardly and somewhat downwardly by a resilient tension spring 527 whose opposite end is fixed with respect to the handgrip by a fixed cross piece 530. Thus, as the lower portion 502 of the trigger 501 is pulled rearwardly toward the handgrip, sequential ones of the trigger teeth 505 catch the tab 523 of the pawl 524 and pivot it upward slightly from its rest position shown in FIG. 14. With the trigger lower portion 502 only partway pulled rearward toward the handgrip, the up-tipped tab 523 blocks forward return of the trigger lower portion 502. It is only after the lower portion 502 of the trigger has been fully pulled rearward that the pawl tab 523 releases the ratchet teeth 505 of the trigger and permits the trigger to return clockwise (FIG. 14) to its relaxed starting position shown in FIG. 14 due to rearward pressure of the compression spring 516 on the spool 514. During this return motion of the trigger, the tab 523 of the pawl 524 is brushed downward from its position shown, by engagement with the trigger ratchet teeth 505 and prevents a reversal of trigger motion until the trigger lower end 502 is fully forward. Accordingly, the pawl 525 requires the trigger to complete its movement in either direction before reversing movement of the trigger is possible. Accordingly, the second slider 464 and any tool driven by the forward end thereof must go through a complete forward stroke before reversing and through a complete rearward stroke before reversing. This is particularly helpful when the tool involved is a staple feeding and forming unit like that at 21E, since it avoids the possibility of jamming of the staple feeding and forming unit 21E by an erroneous reversing of the movement of the second slider prior to completion of the staple feeding and forming cycle.

Thus, it will be seen that one hand H (FIG. 12) of the user can simultaneously (1) grasp the handgrip 421, (2) finger the trigger 501 to actuate a tool, e.g. to feed and form a staple, (3) roll the tube 445 and a tool 412 supported on the front end thereof and (4) change the pitch angle PA of the pitch joint 20E supporting such a tool. This capability is uniquely valuable in a surgical handpiece, wherein the user is typically the surgeon, since it leaves the surgeon's other hand free for other coordinated uses and avoids the need for two hands to manipulate the surgical handpiece.

In the context of a laproscopic hernia stapler, the ability to move about the handle unit 11 is sharply limited by entry of the tube 445 into the surgical site in the patient. Thus it is particularly valuable to be able to change the roll angle and pitch angle of the staple feeding and forming unit 21E, to properly orient and position each successive staple used to close the hernia. To be able to change both pitch and roll rotation of the staple feeding and forming unit 21E and then, as soon as proper orientation and position is achieved, immediately drive the staple with the same hand, is particularly helpful.

While the handle unit 411, embodying the invention above described, is capable of driving a variety of surgical tools 412, by forward/rearward reciprocation of its sliders 463 and 464, the inventive handle unit 411 can for example be used to control a pitch joint unit and staple feeding and forming unit like those of the Ethicon hernia stapler 10E of FIG. 2. While the FIG. 2 Ethicon stapler 10E has been available on the market for some time. Applicants are not aware of a published patent document showing details of its pitch joint 20E and staple feeding and forming unit 21E.

Accordingly, for convenience of the reader, FIGS. 3–7 schematically show aspects of the Ethicon pitch joint unit 20E and FIGS. 8–11C show features of the Ethicon staple feeding and forming unit 21E, such figures being based on inspection of a purchased Ethicon tool of the kind generally shown in FIG. 2.

Tool Example (FIGS. 3–11C)

Turning to the pitch joint unit of FIGS. 3–7, Applicant's tube 445, pitch slider 463 and second slider 464 are adaptable to substitute, for their front end portions, the front end portions of the FIG. 2 tube 16E, pitch slider 23E and second slider 24E. In FIGS. 3–11C, parts of the Ethicon pitch joint unit 20E and staple feeding and forming unit 21E are simplified for convenience in disclosing this on-the-market structural example.

Figure 3:
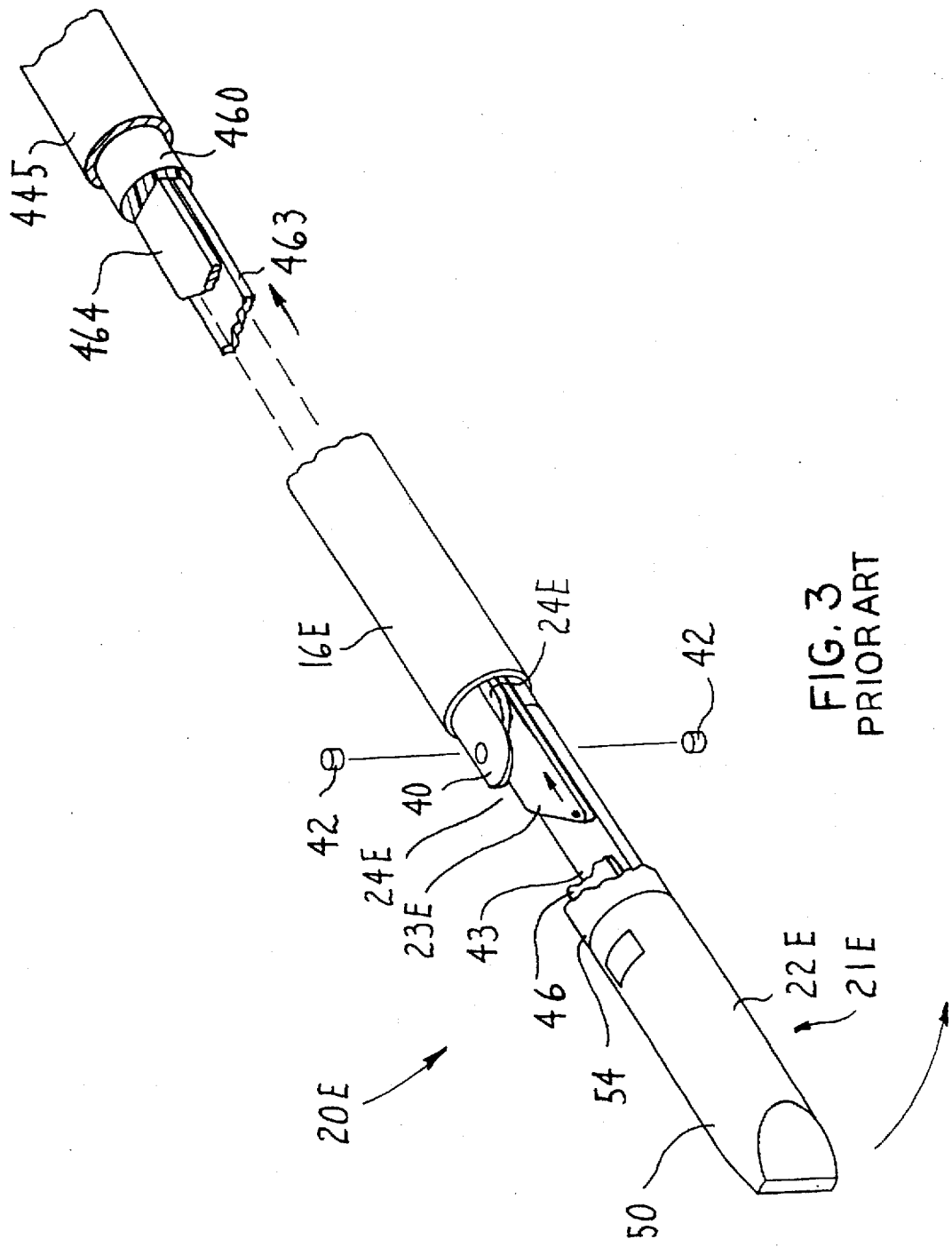
Figure 4:
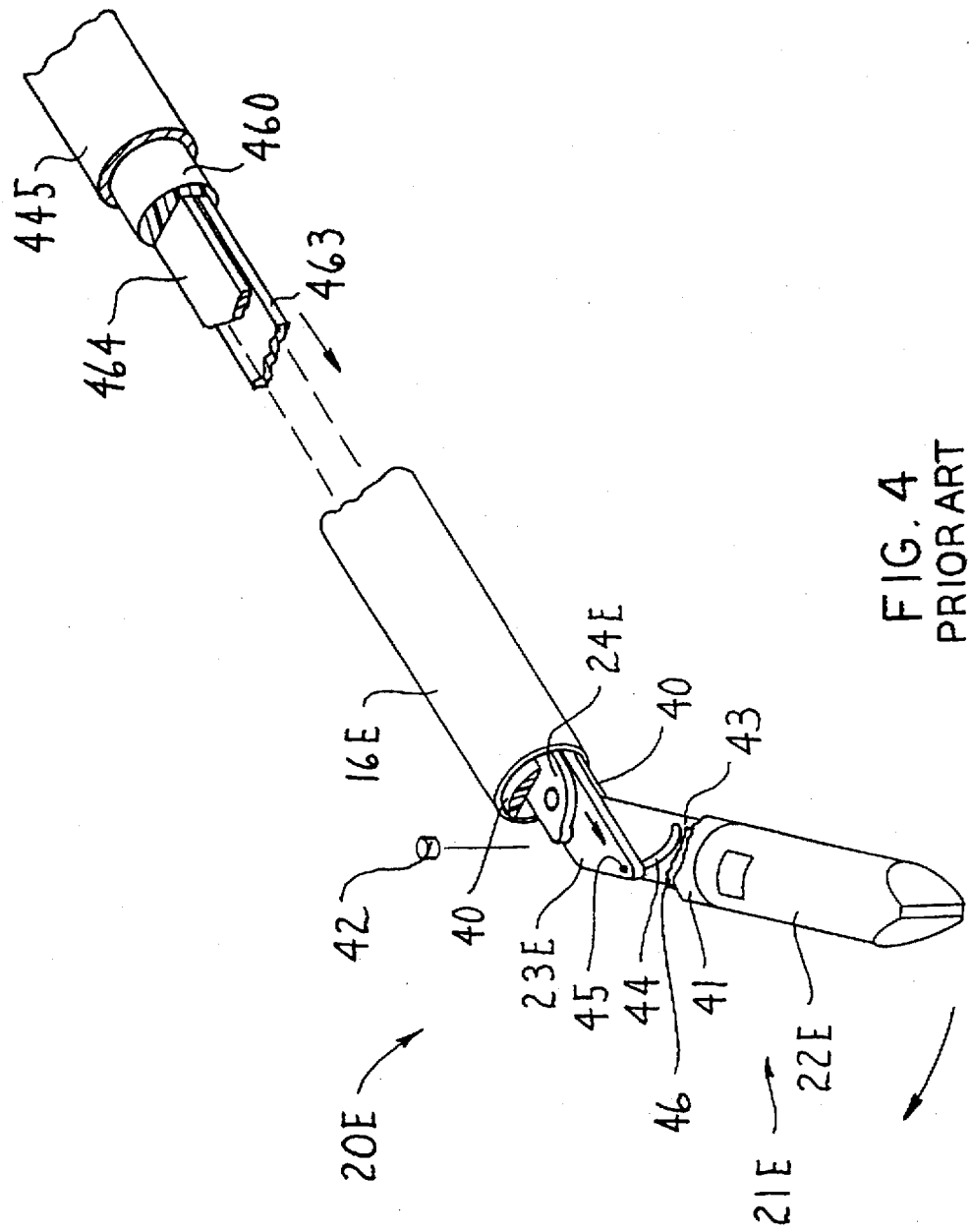

The casing 22E (FIG. 3) is pivoted on the front end of the tube 16E by overlapping pairs of tabs 40 and 41 (FIG. 3). The sliders 23E and 24E are of slidably located between the tab pairs. In the embodiment shown, the tabs 40 extend fixedly forwardly from the tube 16E, and corresponding, longitudinally overlapping tabs 41 extending fixedly rearward from the casing 22e. The free ends of the tabs 40 and 41 in each pair overlap and are pivotally joined by short pins 42 to hinge the casing 22E on the front end of the tube 16E for pivotal movement through the pitch angle PA of FIG. 2. The lower tabs 40 and 41 are not seen in FIGS. 3–7 because they are hidden by other structure, including sliders 23E and 24E. The upper tab 41, while shown in FIG. 4, has its rear end broken away to show the sliders 23E and 24E.

Fixedly extending rearwardly from the casing 22E is a cam plate 43 (FIG. 4) which may be fixed to or even serve as the lower (remote in FIG. 4) tab 41. A curved cam groove 44 in the cam plate 43 receives slidably a camming pin 45 fixed in the tapered front end portion of the pitch slider 23E. Thus, displacement of the pitch slider 23E to its forward position shown in FIG. 3 straightens the apparatus, aligning the casing 22E coaxially with the tube 16E. On the other hand, rearward displacement of the pitch slider 23E to its rearward most position shown in FIG. 4 angles the casing 22E with respect to the tube 16E.

Figure 5:
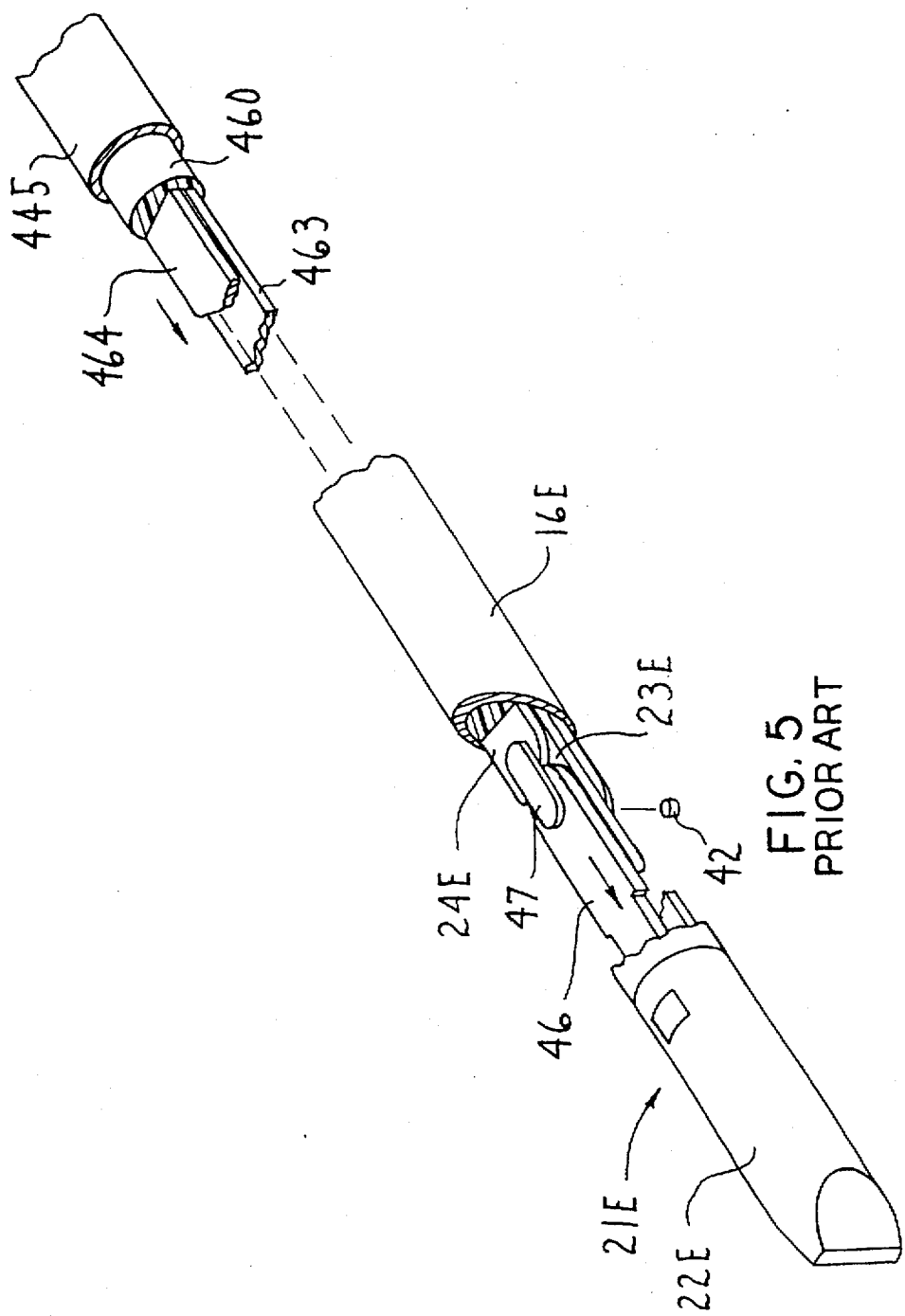
Figure 6:
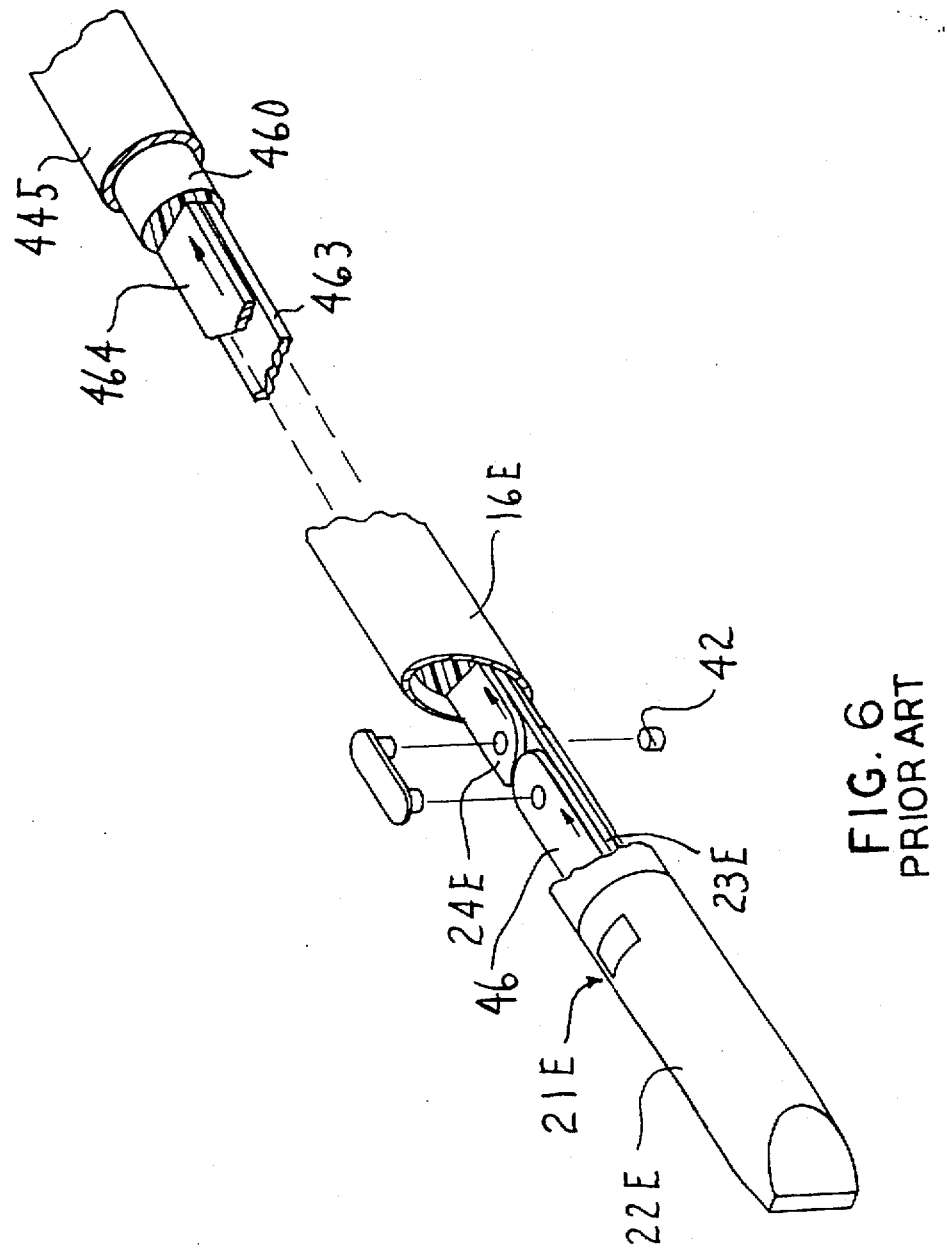
Figure 7:
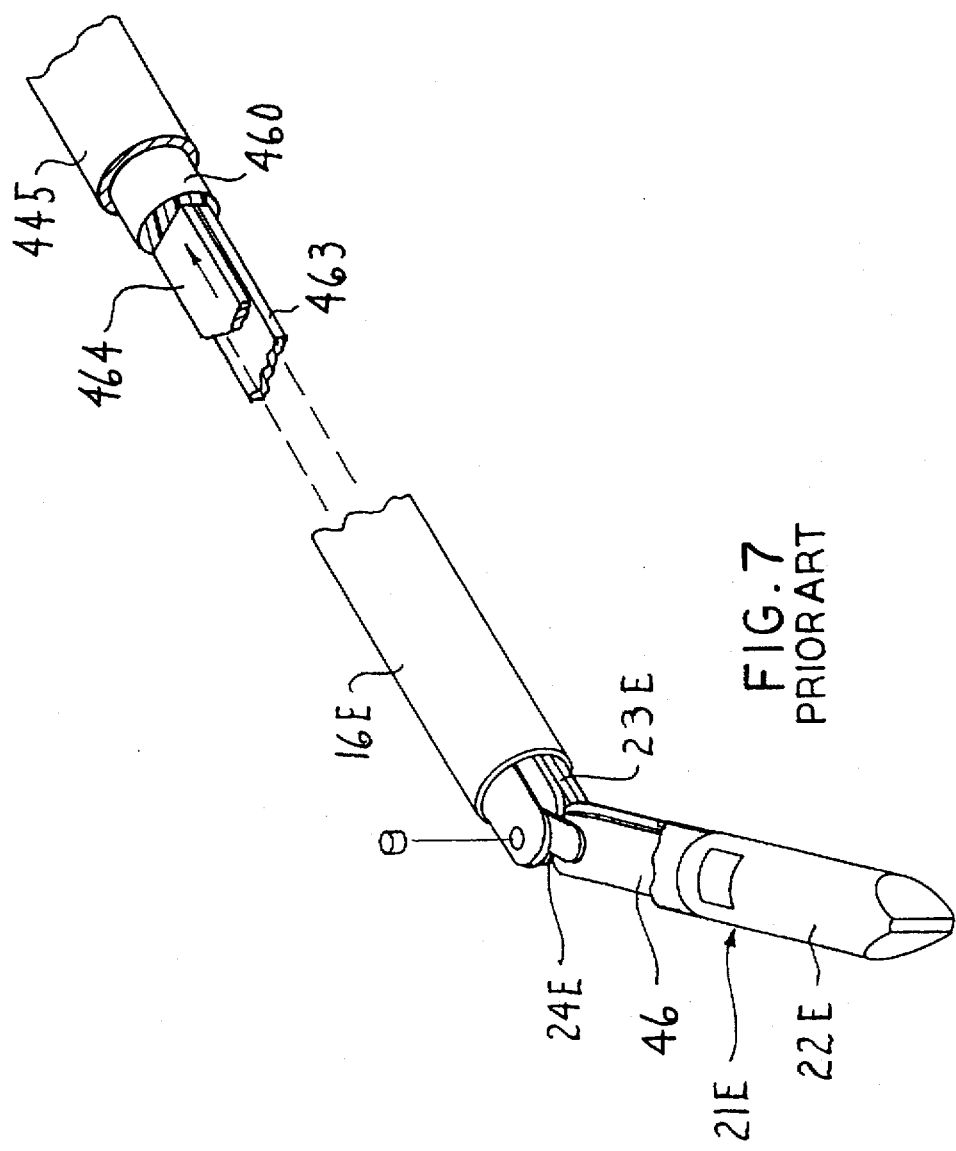

The second slider 24E, as seen in FIGS. 5–7, drives the staple feeding and forming unit 21E. Unit 21E has a rearwardly protruding, axially shiftable staple feeding and forming drive plate 46 parallel to the cam plate 43, for coplanar abutting and pushing forward by the second slider 24E. A two pin, pivot link 47 overlaps and pivotally interconnects adjacent ends of the second slider 24E and drive plate 46 so slider 24E can retract plate 46. Thus, forwarding the second slider 24E cams forward the drive plate 46, as in the transition from FIG. 5 to FIG. 6, to feed and form a staple as hereafter discussed. Same occurs whether the pitch joint unit is in its straight condition of FIGS. 5 and 6, or in its angled condition of FIGS. 4 and 7. With the pitch joint unit 20E angled (bent), the transition from rearward to forward position of the second slider 24 is the transition from FIG. 4 to FIG. 7. The drive plate 46 is broken away in FIGS. 3–7, as above-mentioned, to show the relation of pitch slider 23E to cam plate 43.

Thus, in the example shown in FIGS. 3–7, forwarding of Applicant's pitch slider 463 and second slider 464 forwards pitch slider 23E and second slider 24E, respectively, to thereby change the angle of the casing 22 of the staple feeding and forming unit 21 and fire a staple, respectively.

Figure 8:
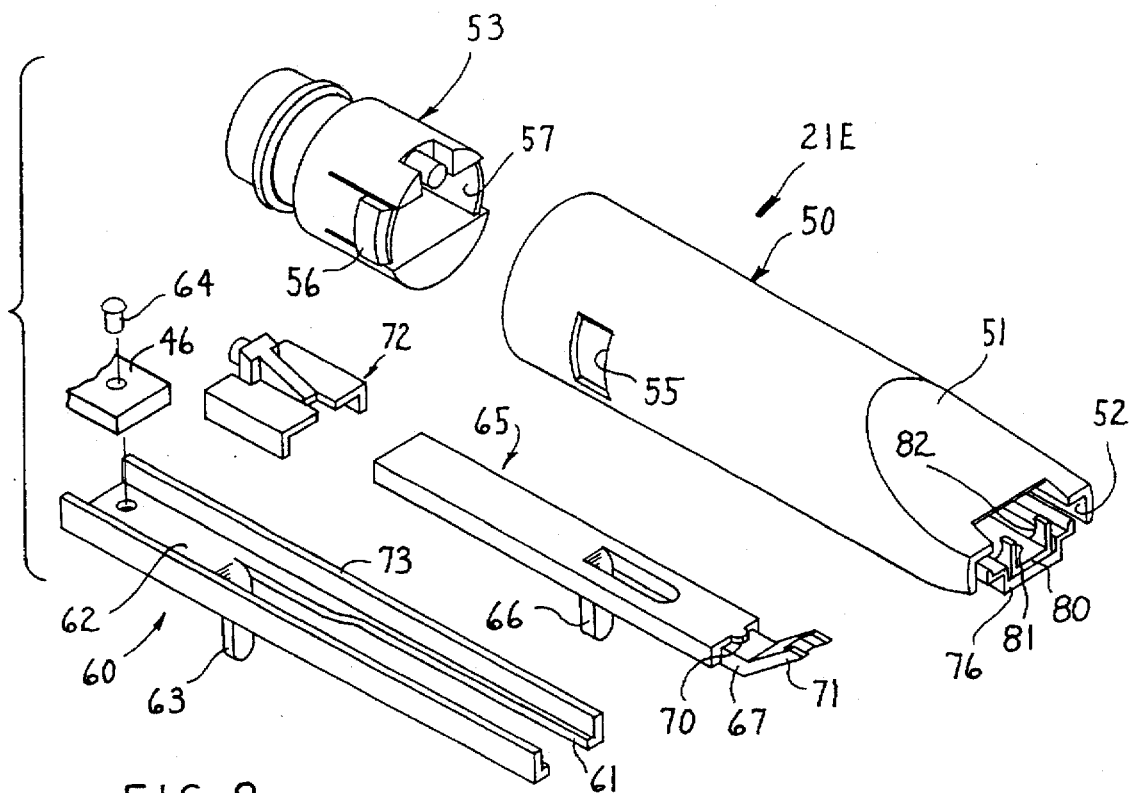
Figure 9:
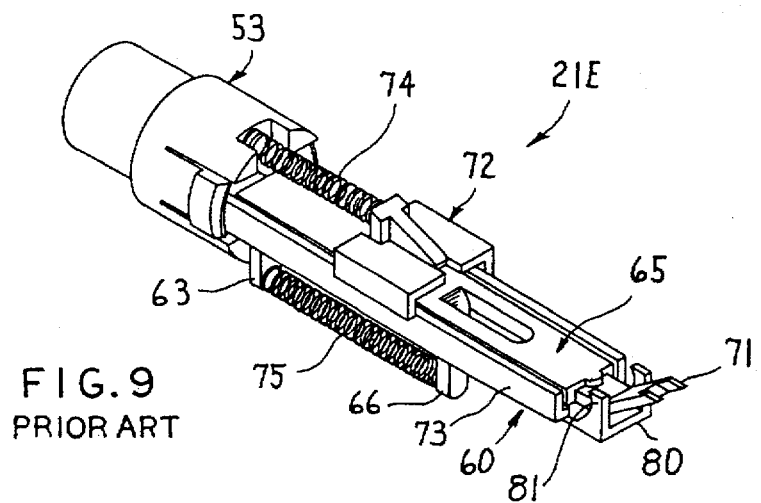
Figure 10A:
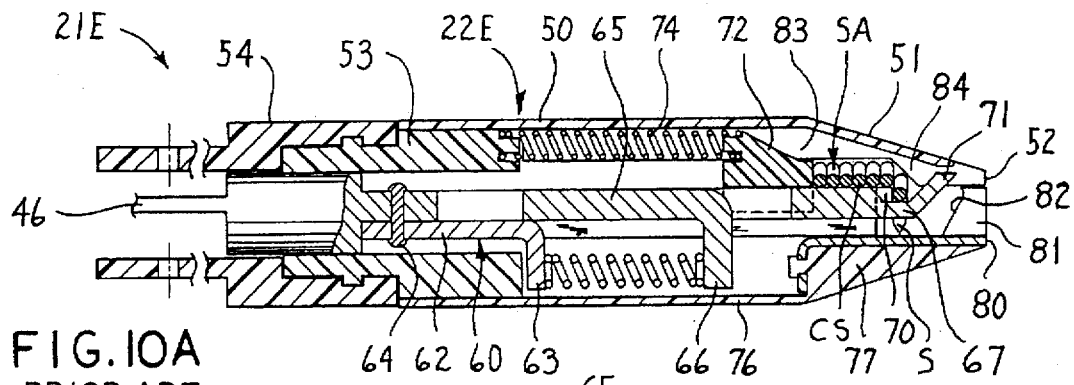
FIGS. 10A and 10B and 10C are enlarged, central cross-sectional views in elevation, showing three successive operating positions of the FIG. 8 unit, for shifting the frontmost staple from its stored, legs depending position to its legs forward position ready for forming.

Turning to the staple feeding and forming unit 21E of FIGS. 8–11C, the casing 22E thereof (FIGS. 8 and 10A)

comprises a substantially clear, generally cylindrical, open ended, rigid plastics case 50. The case 50 is of generally circular perimeter except for a frontal taper defining a generally rectangular open front mouth 52. A stepped annular plug 53 is fixed in the rear end portion of the case 50. An annular elongate carrier 54 fixedly telescopes over the stepped rear end of the annular plug 53 and substantially abuts the rear end of the clear case 50. The carrier 54 extends rearward from the case 50 and, as fragmentarily indicated in FIGS. 3–7, ends in the rearward extending tabs 41 of the pitch joint unit 20E. The tabs 41 thus rigidly support the case 50 and plug 53 in adjustable pitch relation to the tube 16E.

In the embodiment shown, the case 50 has open side windows 55 (FIG. 8) for snap fit receiving leaf spring lugs 56 integrated in the sidewall of the plug 53 to rigidly fix the plug 53 in the rear end of the case 50. The carrier 54 is fixed on the rear end of the plug by means not shown.

The staple feeding and forming unit 21E further includes, within the case 50, an elongate upward opening channel 60 having an elongate front opening notch 61 in the bight 62 thereof, a depending leg 63 set downwardly from the central portion of the bight 62 and means 64 connecting the rear end of the channel fixedly to the front end of the drive plate 46. A staple advancing bar 65 is forwardly/rearwardly slidable in the channel 60 (FIGS. 8 and 9), has a leg 66 upset downwardly from an intermediate portion thereof to depend through the channel notch 61, and has a reduced height and width, forward extending, staple center carrier 67 extending forward therefrom. A forward protruding rounded nose 70 is laterally centered atop the rear portion of the carrier 67. A fork topped ramp 71 extends forward and upward, at an angle, from the staple center carrier 67.

An inverted channel-shaped staple array pusher 72 rides atop the sides 73 of the channel 60, over the top of the bar 65. Coil compression springs 74 and 75 (FIG. 9) respectively (1) press forward the staple array pusher 72 to feed staples one at a time onto the staple center carrier 67 between the nose 70 and ramp 71 (as in FIG. 10A) and (2) press rearward the channel depending leg 63 with respect to the depending bar leg 66. The channel 60 extends forward from the forward facing recess 57 of the plug 53 as seen in FIG. 9. The assembled channel 60, bar 65, pusher 72, and spring 74 and 75 are shown protruding forward from the plug 53 in FIG. 9.

The floor 76 (FIG. 10A) of the case 50 is kicked up to form a platform 77 in the front part of the case 50 and the platform 77 fixedly supports a plate 80 fixedly carrying at its front end an upstanding laterally spaced pair of anvil elements 81. Rear edges 82 of the anvil elements 81 form upstanding, forwardly inclined ramps for formed staple ejection. The front end of the channel 62 rests atop the plate 80 (FIGS. 9 and 10A).

Thus, the above described detailed structure can be more generally summarized as follows. The handpiece 400 (FIG 13) includes a handle unit 411, means carried by the handle unit for engaging a patient (for example the tool 412 at FIG. 12), a hand actuable element mounted for rotation on the handle unit (for example the ball 471), a first means responsive to rotation of the hand actuable element for imparting first degree of freedom movement to the patient engaging means (including in the embodiment shown the rotor 430 of FIG. 22 and tube 445 of FIGS. 12 and 13) and second means responsive to rotation of the hand actuable element for imparting second degree of freedom movement to the patient engaging means (including in the embodiment shown the slider 463 of FIG. 13). Further, the patient engaging means (for example the tool 412 of FIG. 12) may be considered to include a means actuable for applying a fastner to a patient (for example a staple feeding and forming unit like that at 21E in FIG. 2 or for example as detailed in FIGS. 8–11) and means for movably mounting the patient engaging means with respect to the handle (for example the pitch joint unit 20E of FIG. 2 or for example detailed in FIGS. 3–7).

The operation of the unit 21E is briefly summarized below.

FIG. 10A shows the apparatus at rest prior to trigger actuation, and thus prior to forward advancement of the drive plate 46. Staples S each comprise laterally spaced legs LS joined by a bight, the bight having a depress center CS flanked by raised outboard portions OBS. An array SA of staples S rests with portions OBS above the sides 73 of channel 60 and center CS atop the bar 65. The staples S of the array SA are prevented from upward escape and lateral tipping by longitudinally extending, laterally spaced ridges 83 fixedly dependent from the top wall of the case 50 and overlying the bight portions OBS. The pusher 72, forwardly urged by the spring pushes the staple array SA forward against downwardly and forwardly inclined portions 84 of the ridges 83. The ridges 83 are laterally spaced apart in a symmetric manner to approximately overlie the sides 73 of the channel 60. As here shown, the ridge portions 84 are located to allow the frontmost staple S to move forward off the nose 70 and drop onto the staple center carrier 67.

Figure 10B:
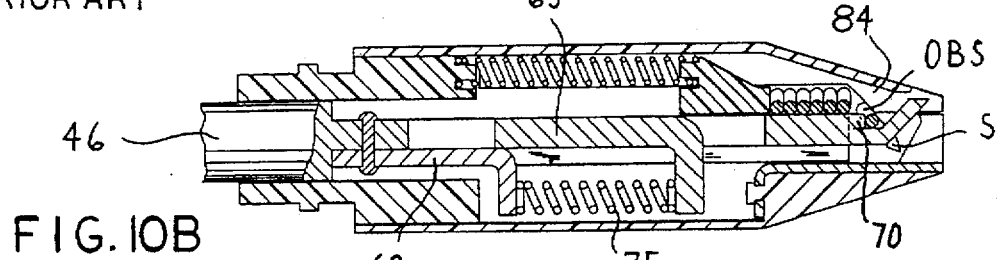
Figure 10C:
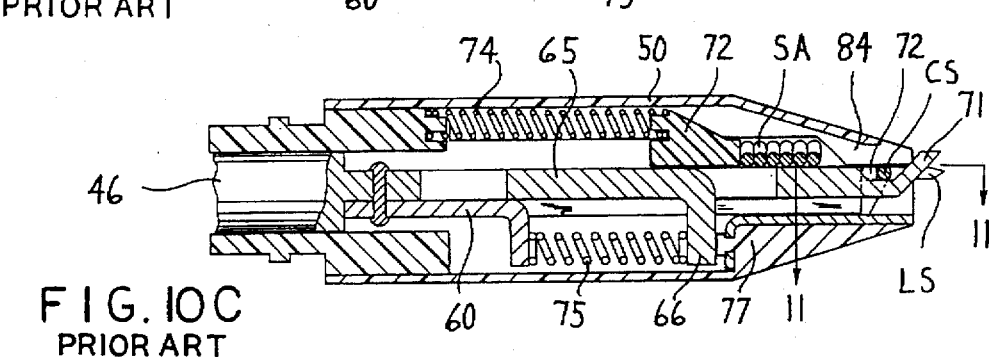

The first part of rearward movement of the trigger 501, and resulting forward movement of sliders 464 and 24E and drive plate 46, as shown in FIG. 10B, slightly forwards the channel 60 and, through the lower spring 75, the bar 65. The thus slightly forwarded nose 70 pushes the center CS of the front staple S correspondingly slightly forward while the depending ramp portions 84 (FIG. 10B) blocks corresponding forward movement of the raised outboard portions OBS (FIG. 11A) of the staple S, to cause the staple S to start pivoting counterclockwise as in FIG. 10B.

Further rearward displacement of the trigger and resulting further forward displacement of the second sliders 464 and 24E and drive plate 46 further forwards the channel 60 and, through the spring 75, the bar 65, until the depending bar leg 66 is stopped by abutment with the rear end of the platform 77, and the depending ramp portion 84 has tipped the staple S counter-clockwise through 90°, so that the laterally spaced legs LS of the staples protrude forwardly, rather than downwardly. During this transition of a parts forwardly from FIG. 10A to FIG. 10C, the ramp portions 84 with their rear facing edges have prevented corresponding forward advancement of the staple array SA, as permitted by the resilience of the spring 74 backing the pusher 72.

Figure 11A:
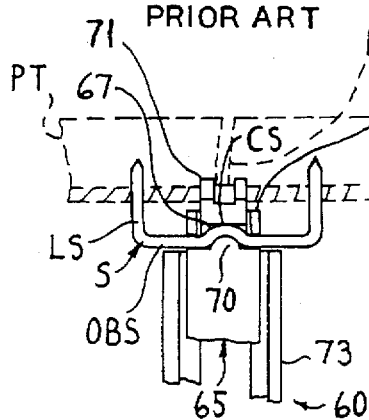

At this point, the forward extending legs LS of the staple S can be inserted into patient tissue shown in dotted line at PT in FIG. 11A, on opposite sides of a hernial tear HT to be mended.

Figure 11B:
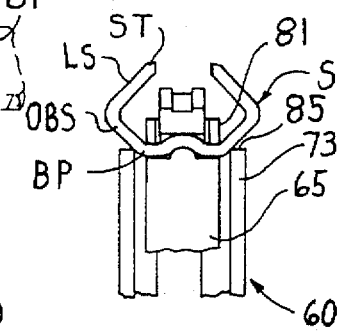

Further displacement rearward of the trigger and forward of the second sliders 464 and 24E and drive plate 46 advances further forward the channel 60 with respect to the stopped bar 65 and anvil elements 81 fixedly carried by the case 50. The result as shown in FIG. 11b wherein the forward advancing front ends 85 of the channel sides 73 engage the outboard portions OBS of the staple bight and bends same forwardly around the anvil elements 81 which the channel sides 73 are about to flank. The resulting bends in the staple bight are indicated at BP in FIG. 11B. FIG. 11B also shows that the initially parallel staple legs LS are now beginning to converge forwardly so their sharpened tips ST are coming together.

Figure 11C:
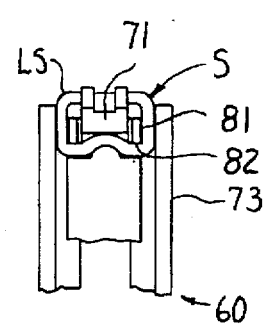

Completion of forward movement of the second sliders 464 and 24E and drive plate 46 and channel 60 is shown in FIG. 11C, wherein the channel sides 73 now more than flank the anvil elements 81, and have closed the stapler S to a substantially rectangular shape with the legs LS somewhat overlapping each other a first staple in the patient tissue PT to join opposite sides of the hernial tear HT. At this point, the trigger is normally released by the surgeon, allowing the second sliders 464 and 24E and drive plate 46 to return rearwardly to their starting position. During this return the thus closed (formed) staple S is allowed to slide up off the ramp 71 of the retreating bar 65.

As the bar returns to its rearwardmost position, the upper spring 74 causes the pusher 72, as permitted by a small space between the depending ridge portion 84 and the nose 70, to push a second staple S to drop onto the staple center carrier 67.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical handpiece comprising:
    a handle unit;
    means carried by said handle unit for engaging a patient;
    a hand actuable element mounted on said handle unit for rotation relative to said handle unit about first and second mutually transverse axes;
    first means operatively connected to said hand actuable element and responsive to rotation of said hand actuable element relative to said handle unit about said first axis for imparting first degree of freedom movement to said patient engaging means;
    second means operatively connected to said hand actuable element and responsive to rotation of said hand actuable element relative to said handle unit about said second axis for imparting second degree of freedom movement to said patient engaging means.

2. The apparatus of claim 1 in which said handle unit comprises a barrel and a handgrip fixedly joined adjacent a rear end portion of said barrel, means mounting said hand actuable element substantially at the join of said barrel and handgrip for single hand actuation, said hand actuable element having exposed outer surface means for actuating engagement by a thumb of a person's hand gripping said handgrip.

3. The apparatus of claim 1 in which said hand actuable element is a ball and said first and second axes intersect said ball.

4. A surgical handpiece comprising:
    a handle unit;
    means carried by said handle unit for engaging a patient;
    a hand actuable element mounted for rotation on said handle unit about first and second mutually transverse axes;
    first means operatively connected to said hand engagable element and responsive to rotation of said hand actuable element about said first axis for imparting first degree of freedom movement to said patient engaging means;
    second means operatively connected to said hand engagable element and responsive to rotation of said hand actuable element about said second axis for imparting second degree of freedom movement to said patient engaging means, said handle unit comprising a barrel and a handgrip fixed adjacent a rear end portion of said barrel, said hand actuable element comprising a convexly rounded element located for single hand actuation substantially at the juncture of said barrel and handgrip, said rounded element having an exposed outer surface engageable by a thumb of a person's hand gripping said handgrip.

5. The apparatus of claim 4 in which said patient engaging means comprises means actuable for applying a fastener to a patient, means for movably mounting said patient engaging means on said handle unit, said first rotation responsive means comprising a first member moveable with respect to said handle unit and connected to said patient engaging means for imparting roll movement thereto, said second rotation responsive means comprising a second member moveable with respect to said handle unit and connected to said patient engaging means for imparting pitch movement thereto.

6. The apparatus of claim 5 in which said fastener applying means comprises means for feeding a staple and forming such staple in engagement with patient tissue.

7. A surgical handpiece comprising:
    a handle unit;
    means carried by said handle unit for engaging a patient;
    a hand actuable element mounted for rotation on said handle unit about first and second mutually transverse axes;
    first means operatively connected to said hand engagable element and responsive to rotation of said hand actuable element about said first axis for imparting first degree of freedom movement to said patient engaging means;
    second means operatively connected to said hand engagable element and responsive to rotation of said hand actuable element about said second axis for imparting second degree of freedom movement to said patient engaging means, said handle unit comprising a barrel and handgrip fixed adjacent a rear end portion of said barrel, said hand actuable element comprising a ball swivelly located adjacent the juncture of said barrel and handgrip for rotation sideways about said first axis and forward about said second axis.

8. The apparatus of claim 7 in which said handle unit is hollow and defines a chamber therein, said ball being located in and partly protruding from a portal in said housing substantially at the juncture of said barrel and handgrip, said ball being hollow and having a recess open to said handle chamber, said first rotation responsive means comprising an elongate rotor extending longitudinally in, and substantially the length of, said barrel and supported therein for roll rotation about said first axis, shaft means transversely mounted on a rear end portion of said rotor and substantially diametrally mounting said ball for pitch rotation with respect to said rotor and about said second axis.

9. The apparatus of claim 8 in which said first rotation responsive means comprises an elongate tube fixed at a rear end thereof coaxially to said rotor and extending forwardly from said rotor and barrel for roll rotation therewith, pitch pivot means for mounting said patient engaging means for pitch rotation on a front end of said tube, said second rotation responsive means comprising an elongate pitch slider which is roll rotatable with and longitudinally slidable in said tube, eccentric means fixed on said ball for at least pitch rotation therewith and connected to a rear end portion of said pitch slider for moving said pitch slider longitudinally in said tube upon pitch rotation of said ball, means connecting a front end portion of said pitch slider to said patient engaging means for pitch rotation of said patient engaging means with respect to said tube.

10. The apparatus of claim 9 in which said rotor and pitch slider have rear end portions extending into said recess in said ball, said shaft means comprising a first shaft extending diametrally across said ball recess and through said rear end portion of said rotor, said eccentric means comprising a second shaft parallel to and located below said first shaft and engaging said rear end portion of said pitch slider so pitch rotation of said ball reciprocates said pitch slider longitudinally with respect to said rotor and in said tube.

11. The apparatus of claim 9 including a spool coaxially surrounding and axially slidable on said rotor, means for causing said spool to rotate with said rotor, spring means for urging said spool rearwardly with respect to said rotor and barrel, a trigger movably mounted on said handle and actuable by a hand holding said handle for axially sliding said spool with respect to said handle, a second elongate slider roll rotatable with and longitudinally slidable in said tube beside said pitch slider, means connecting said patient engaging means to a front end portion of said second slider for actuating said patient engaging means to treat tissue of a patient engaged thereby.

12. The apparatus of claim 11 in which said patient engaging means comprises staple forming means actuable by said second slider for stapling patient tissue.

13. The apparatus of claim 11 in which said trigger has a lower end portion actuable by a hand holding said handle, an upper end engageable with said spool, a rearwardly extending arm with ratchet teeth, and a pivot intermediate said trigger ends and for pivoting said trigger with respect to said handle, a pawl pivotable on said handle and extending forward to engage said ratchet teeth on said trigger, resilient biasing means biasing said pawl with respect to said handle to block reversal of movement of said trigger except at opposite ends of said trigger stroke.

14. A surgical apparatus for installing fasteners particularly for use in endoscopic surgery, comprising:
means for forming a fastener in contact with body tissue of a patient in a surgical procedure;
a handle unit comprising a frame and a multi-pivot member pivotable about first and second mutually transverse axes with respect to said frame in response to actuation by surgical personnel;
a coupling unit supporting said fastener forming means distally of said handle unit and comprising first and second means respectively responsive to pivoting of said multi-pivot member about said first and second axis for displacing said fastener forming means in respective different first and second degrees of freedom with respect to said handle unit, in which said multi-pivot member is generally ball-shaped and said pivot axes intersect substantially at the center of the curvature of said ball shape.

15. The apparatus of claim 14 in which said coupling unit includes a forward extending tube and means for supporting said tube on said frame for rotation about a roll axis defined by a longitudinal, forward extending axis of said tube, means connecting said multi-pivot member to said tube for roll motion therewith, such that roll motion of said multi-pivot member imparts roll motion to said tube, said multi-pivot member being pivotable with respect to said tube about a pitch axis, said roll axis and said pitch axis constituting said first and second mutually transverse axes of said multi-pivot member.

16. The apparatus of claim 15 in which said first means includes said tube, said second means comprising a generally forward extending rod longitudinally receivable in said tube, said first and second degrees of freedom respectively comprising roll pivoting about said longitudinal axis of said tube and pitch pivoting about said axis.

17. The apparatus of claim 14 in which said multi-pivot member is rigid with said first and second axes oriented for side to side and forward/rearward pivoting movement.

18. The apparatus of claim 17 in which one of said axes extends along a length of the apparatus and the other of said axes extends sideways of the apparatus, said axes intersecting.

19. The apparatus of claim 14 in which said frame comprises a substantially gun shaped housing having a forward extending barrel and a depending handgrip adjacent a rear end of said barrel, said ball-shaped member being located adjacent the intersection of said barrel and handgrip and adjacent said rear end of said barrel.

20. The apparatus of claim 19 in which said ball-shaped member is exposed rearwardly, sidewardly and upwardly for engagement by a thumb of a hand holding the handgrip.

21. A handle unit for a surgical handpiece, the handle unit comprising:
a hand actuable element mounted on said handle unit for rotation relative to said handle unit about first and second mutually transverse axes;
first means operatively connected to said hand actuable element and responsive to rotation of said hand actuable element relative to said handle unit about said first axis for imparting first degree of freedom movement to a patient engaging means;
second means operatively connected to said hand actuable element and responsive to rotation of said hand actuable element relative to said handle unit about said second axis for imparting second degree of freedom movement to a patient engaging means.

22. A surgical apparatus for installing fasteners particularly for use in endoscopic surgery, comprising:
means for forming a fastener in contact with body tissue of a patient in a surgical procedure;
a handle unit comprising a frame and a multi-pivot member pivotable about first and second mutually transverse axes with respect to said frame in response to actuation by surgical personnel;
a coupling unit supporting said fastener forming means distally of said handle unit and comprising first and second means respectively responsive to pivoting of said multi-pivot member about said first and second axis for displacing said fastener forming means in respective different first and second degrees of freedom with respect to said handle unit, said multi-pivot member comprising a ball, said first means comprising a tube extending forward from said frame along said first axis and supported for roll pivoting on said frame about said first axis, means pivotally mounting said ball with respect to a rear portion of said tube for roll pivoting therewith about said first axis and for pitch pivoting with respect thereto about said second axis, said second means comprising a rod extending longitudinally and slidably in said tube and coupled adjacent its rear end with respect to transverse pivot means on said ball.

23. A surgical apparatus for installing fasteners particularly for use in endoscopic surgery, comprising:

means for forming a fastener in contact with body tissue of a patient in a surgical procedure;

a handle unit comprising a frame and a multi-pivot member pivotable about first and second mutually transverse axes with respect to said frame in response to actuation by surgical personnel;

a coupling unit supporting said fastener forming means distally of said handle unit and comprising first and second means respectively responsive to pivoting of said multi-pivot member about said first and second axes for displacing said fastener forming means in respective different first and second degrees of freedom with respect to said handle unit.

24. A handle unit for a surgical handpiece, the handle unit comprising:

a hand actuable element mounted for rotation on said handle unit about first and second mutually transverse axes;

first means operatively connected to said hand engagable element and responsive to rotation of said hand actuable element about said first axis for imparting first degree of freedom movement to a patient engaging means;

second means operatively connected to said hand engagable element and responsive to rotation of said hand actuable element about said second axis for imparting second degree of freedom movement to a patient engaging means, said handle unit comprising a handgrip engageable by a palm and one or more fingers of a hand of a user, a trigger unit movable toward and away from the handgrip and engageable by a finger of the hand of the user, said hand actuable element comprising a ball mounted for rotation about said first and second axes above a palm engageable portion of said handgrip for engagement by a thumb of the hand of the user, means carried by said handgrip and extending forward therefrom for engaging a patient and comprising a tube and first and second sliders slidable longitudinally side by side along and within said tube, said first means including means responsive to rotation of said ball about said first axis for imparting roll rotation to said tube, said second means including means responsive to rotation of said ball about said second axis for imparting longitudinal sliding motion to first said slider, means connecting said trigger to said second slider for longitudinal sliding motion of said second slider in response to movement of said trigger.

* * * * *